United States Patent
Kim

(10) Patent No.: US 10,588,209 B2
(45) Date of Patent: *Mar. 10, 2020

(54) MOBILE X-RAY APPARATUS AND METHOD OF OPERATING THE SAME

(71) Applicant: SAMSUNG ELECTRONICS CO., LTD., Suwon-si (KR)

(72) Inventor: Myeong-je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/031,747

(22) Filed: Jul. 10, 2018

(65) Prior Publication Data

US 2018/0332696 A1 Nov. 15, 2018

Related U.S. Application Data

(63) Continuation-in-part of application No. 15/392,044, filed on Dec. 28, 2016, now Pat. No. 10,051,718.

(30) Foreign Application Priority Data

Aug. 3, 2016 (KR) .......................... 10-2016-0099135
Dec. 28, 2016 (KR) .......................... 10-2016-0181362

(51) Int. Cl.
*H05G 1/54* (2006.01)
*A61B 6/00* (2006.01)

(52) U.S. Cl.
CPC ............. *H05G 1/54* (2013.01); *A61B 6/4405* (2013.01); *A61B 6/54* (2013.01); *A61B 6/56* (2013.01)

(58) Field of Classification Search
None
See application file for complete search history.

(56) References Cited

U.S. PATENT DOCUMENTS

| | | | |
|---|---|---|---|
| 4,797,907 A | 1/1989 | Anderton | |
| 7,029,819 B2 | 4/2006 | Laney et al. | |
| 9,166,399 B2 | 10/2015 | Lei | |
| 9,554,768 B2 | 1/2017 | Kim | |
| 10,051,718 B2 * | 8/2018 | Kim ..................... | A61B 6/4405 |

(Continued)

FOREIGN PATENT DOCUMENTS

| CN | 105044765 A | 11/2015 |
|---|---|---|
| CN | 105326515 A | 2/2016 |

(Continued)

OTHER PUBLICATIONS

Communication dated Feb. 13, 2018, issued by the Korean Intellectual Property Office in counterpart Korean application No. 10-2016-0181362.

(Continued)

*Primary Examiner* — Hoon K Song
(74) *Attorney, Agent, or Firm* — Sughrue Mion, PLLC

(57) ABSTRACT

A mobile X-ray apparatus is configured to control an operation of a protection circuit for protecting the lithium ion battery during X-ray emission, and a method of operating the mobile X-ray apparatus is disclosed. In detail, the mobile X-ray apparatus is capable of preventing a protection circuit from operating for a preset time starting from a time point when an X-ray emission preparation signal is received.

13 Claims, 12 Drawing Sheets

(56) References Cited

U.S. PATENT DOCUMENTS

| | | |
|---|---|---|
| 2011/0254515 A1 | 10/2011 | Hara et al. |
| 2011/0267726 A1 | 11/2011 | Ikeuchi et al. |
| 2011/0280374 A1 | 11/2011 | Ohta et al. |
| 2012/0169284 A1 | 7/2012 | Park |
| 2012/0268066 A1 | 10/2012 | Endo et al. |
| 2012/0294428 A1 | 11/2012 | Oketa et al. |
| 2014/0159670 A1 | 6/2014 | Lee et al. |
| 2014/0308546 A1 | 10/2014 | Niederl |
| 2015/0294826 A1 | 10/2015 | Kim et al. |
| 2015/0380924 A1 | 12/2015 | Ohwaki et al. |
| 2016/0064776 A1 | 3/2016 | Ro |
| 2016/0191049 A1 | 6/2016 | Lee et al. |

FOREIGN PATENT DOCUMENTS

| | | |
|---|---|---|
| EP | 2774541 A1 | 3/2014 |
| EP | 2865333 A1 | 4/2015 |
| JP | 6-105458 A | 4/1994 |
| JP | 2003-32801 A | 1/2003 |
| JP | 2016-73102 A | 5/2016 |
| KR | 10-2008-0112844 A | 12/2008 |
| KR | 10-2012-0078842 A | 7/2012 |
| KR | 10-1428262 B1 | 8/2014 |
| KR | 10-2015-0047749 A | 5/2015 |
| KR | 10-2016-0024603 A | 3/2016 |

OTHER PUBLICATIONS

Communication dated Aug. 18, 2017, issued by the Korean Intellectual Property Office in counterpart Korean Patent Application No. 10-2016-0181362.

Communication dated Jun. 19, 2017, issued by the European Patent Office in counterpart European Patent Application No. 17162664.1.

Communication dated Oct. 21, 2019, issued by the State Intellectual Property Office of P.R. China in counterpart Chinese Application No. 201710590004.3.

* cited by examiner

MOBILE X-RAY APPARATUS AND METHOD OF OPERATING THE SAME

CROSS-REFERENCE TO RELATED APPLICATIONS

This application is based on and claims priority to Korean Patent Application No. 10-2016-0099135, filed on Aug. 3, 2016, Korean Patent Application No. 10-2016-0181362, filed on Dec. 28, 2016 in the Korean Intellectual Property Office, and U.S. application Ser. No. 15/392,044, filed Dec. 28, 2016, the disclosures of which are incorporated herein in their entirety by reference.

BACKGROUND

1. Field

The present disclosure relates to mobile X-ray apparatuses including lithium ion batteries and methods of operating the mobile X-ray apparatuses.

2. Description of the Related Art

X-rays are electromagnetic waves having wavelengths of 0.01 to 100 angstroms (Å), and are widely used, due to their ability to penetrate objects, in medical apparatuses for imaging the inside of a living body or in non-destructive testing equipment for industrial use.

An X-ray apparatus using X-rays may obtain X-ray images of an object by transmitting X-rays emitted from an X-ray source through an object and detecting a difference in intensities of the transmitted X-rays via an X-ray detector. The X-ray images may be used to examine an internal structure of an object and diagnose a disease of the object. The X-ray apparatus facilitates observation of an internal structure of an object by using a principle in which penetrating power of an X-ray varies depending on the density of the object and atomic numbers of atoms constituting the object. As a wavelength of an X-ray decreases, penetrating power of the X-ray increases and an image on a screen becomes brighter.

SUMMARY

Provided are mobile X-ray apparatuses including lithium ion batteries and methods of operating the mobile X-ray apparatuses.

Additional aspects will be set forth in part in the description which follows and, in part, will be apparent from the description, or may be learned by practice of the presented embodiments.

According to an aspect of an embodiment, a mobile X-ray apparatus includes: an X-ray radiator; a controller configured to control the X-ray radiator; and a power supply including a lithium ion battery configured to supply an operating power to the X-ray radiator and the controller and a battery management system (BMS) configured to control an operation of a protection circuit for protecting the lithium ion battery.

The BMS is further configured to change, during X-ray emission by the X-ray radiator, reference values for operating the protection circuit against overcurrent.

The BMS is further configured to change, during X-ray emission by the X-ray radiator, a reference value for operating the protection circuit against over-discharge.

The BMS is further configured to increase, based on an X-ray emission preparation signal, an overcurrent reference value for operating the protection circuit and decrease an over-discharge reference value for operating the protection circuit.

The BMS is further configured to respectively change, based on an X-ray emission completion signal, the changed overcurrent reference value and the changed over-discharge reference value back to the same overcurrent and over-discharge reference values as before.

The BMS is further configured to prevent the protection circuit from protecting against at least one of overcurrent and over-discharge during the X-ray emission by the X-ray radiator.

The BMS is further configured to control the operation of the protection circuit protecting against at least one of over-discharge, overcurrent, overheating, and unbalancing between cells in the lithium ion battery, and control the operation of the protection circuit protecting against the at least one exceptionally during the X-ray emission.

The mobile X-ray apparatus may further include a charger configured to charge the lithium ion battery, and the charger is further configured to control charging of the lithium ion battery during the X-ray emission by the X-ray radiator.

The charger is further configured to stop the charging of the lithium ion battery based on an X-ray emission preparation signal.

The charger is further configured to resume the charging of the lithium ion battery based on an X-ray emission completion signal.

The mobile X-ray apparatus may further include a first current sensor for detecting current having a relatively low intensity and a second current sensor for detecting current having a relatively high intensity, and the BMS is further configured to detect, during the X-ray emission by the X-ray radiator, overcurrent caused by the X-ray emission by using the second current sensor.

The BMS is further configured to activate the second current sensor and deactivate the first current sensor based on an X-ray emission preparation signal.

The BMS is further configured to activate the first current sensor and deactivate the second current sensor based on an X-ray emission completion signal.

The BMS and the controller may respectively include communication interfaces and communicate with each other via the communication interfaces.

According to another aspect of an embodiment, a method of operating a mobile X-ray apparatus including a lithium ion battery includes: receiving an X-ray emission command from a user; and controlling, during X-ray emission, an operation of a protection circuit for protecting the lithium ion battery.

According to another aspect of an embodiment, a mobile X-ray apparatus includes: an X-ray radiator; a controller configured to control the X-ray radiator; a lithium ion battery configured to supply an operating power to the X-ray radiator and the controller; a protection circuit configured to protect the lithium ion battery against overcurrent or over-discharge; and a battery management system (BMS) configured to control an operation of the protection circuit based on status information of the lithium ion battery, wherein the BMS is further configured to receive an X-ray emission preparation signal from the controller and prevent the protection circuit from operating during a preset time period starting from a time point at which the X-ray emission preparation signal is received by the BMS.

The BMS may be further configured to resume the operation of the protection circuit when the preset time period ends.

The controller may be further configured to control the X-ray radiator to complete X-ray emission before a second time point that occurs the preset time period after a first time point at which the X-ray emission preparation signal is transmitted to the BMS.

The BMS may be further configured to receive an X-ray emission completion signal from the controller before the second time point.

The mobile x-ray apparatus may further include at least one capacitor configured to charge an internal charge (i.e., be charged) by using a power from the lithium ion battery and supply a power to the X-ray radiator by using a discharge voltage.

The at least one capacitor may be further configured to supply the power to the X-ray radiator by using the discharge voltage while the X-ray radiator emits X-rays toward an object based on the X-ray emission preparation signal received from the controller.

Each of the at least one capacitor may have a capacitance less than or equal to 10,000 micro-farads (μF).

The at least one capacitor may include two capacitors.

The BMS and the controller may each include a communication interface and the BMS and the controller may communicate with each other via the communication interfaces.

According to another aspect of an embodiment, a method of operating a mobile X-ray apparatus comprising a lithium ion battery includes: receiving an instruction for X-ray emission from a user; preventing a protection circuit from protecting the lithium ion battery during a preset time period starting from a time point at which the instruction is received; and emitting X-rays toward an object based on the received instruction.

The method may further include resuming an operation of the protection circuit after a time point that occurs when the preset time period ends.

The emitting of the X-rays toward the object may include completing the X-ray emission before a time point that occurs the preset time period after the time point at which the instruction is received.

According to another aspect of an embodiment, a computer program product includes a non-transitory computer-readable storage medium having recorded thereon a method of operating a mobile X-ray apparatus including a lithium ion battery, wherein the non-transitory computer-readable storage medium includes instructions which, when executed by the mobile X-ray apparatus, cause the mobile X-ray apparatus to perform the method including: receiving an instruction for X-ray emission from a user; preventing a protection circuit from protecting the lithium ion battery during a preset time period from a time point at which the instruction is received; and emitting X-rays toward an object based on the received instruction.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
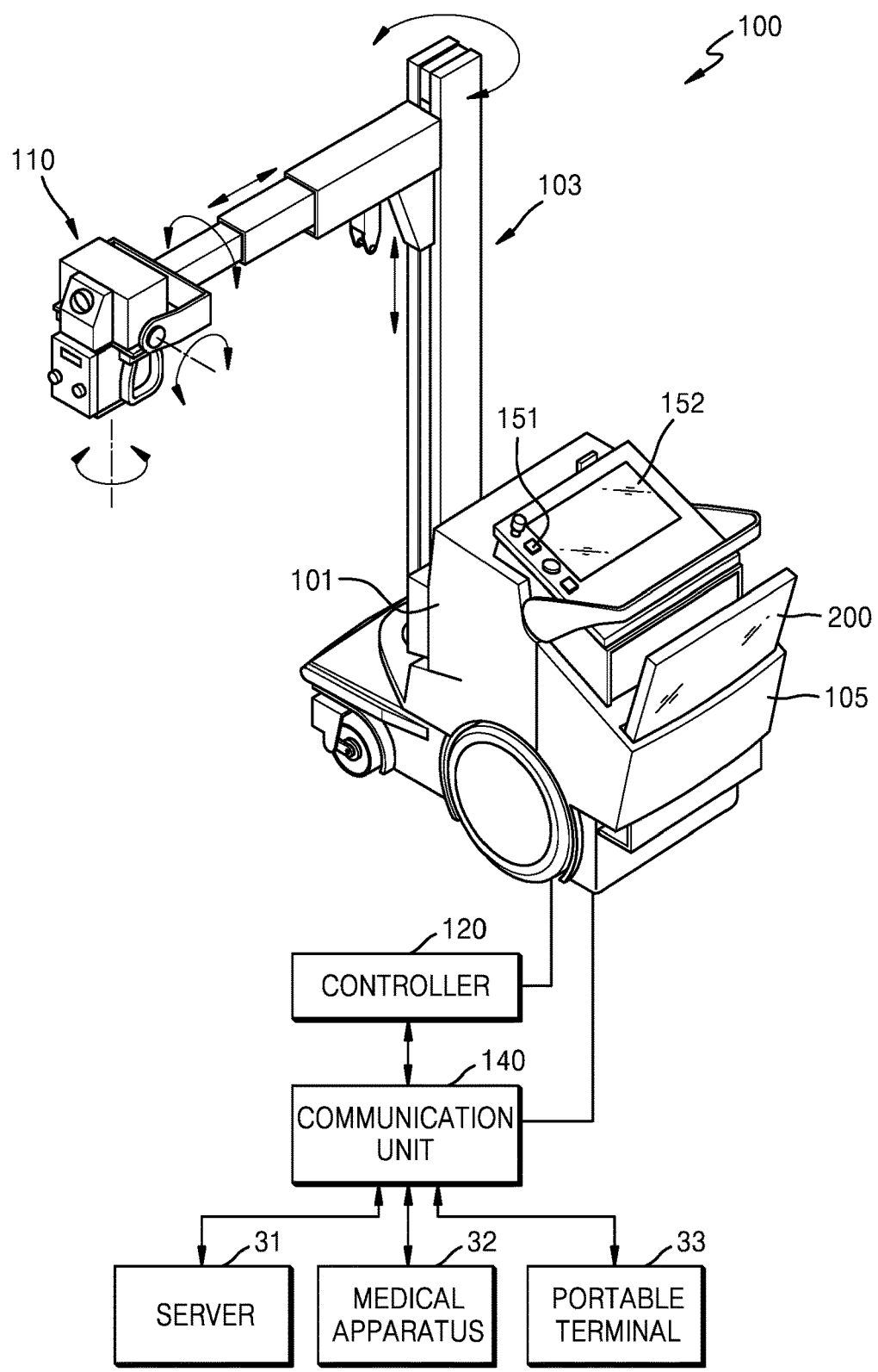
FIG. 1 is an external view and block diagram of an X-ray apparatus implemented as a mobile X-ray apparatus, according to an embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. The term "part" or "portion" used herein may be implemented using hardware or software, and according to embodiments, a plurality of "parts" or "portions" may be formed as a single unit or element, or one "part" or "portion" may include a plurality of units or elements. As used herein, the term "and/or" includes any and all combinations of one or more of the associated listed items. Expressions such as "at least one of," when preceding a list of elements, modify the entire list of elements and do not modify the individual elements of the list. Hereinafter, the operating principles and embodiments of the present disclosure will be described in detail with reference to the accompanying drawings.

In the present specification, an image may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and include a human, an animal, or a part of a human or animal. For example, the object may include a body part (an organ, etc.) or a phantom.

FIG. 1 is an external view and block diagram of an X-ray apparatus 100 implemented as a mobile X-ray apparatus, according to an embodiment.

Referring to FIG. 1, the X-ray apparatus 100 according to the present embodiment includes an X-ray radiator 110 for generating and emitting X-rays, an input device 151 for receiving a command from a user, a display 152 for providing information to the user, a controller 120 for controlling the X-ray apparatus 100 according to the received command, and a communication unit 140 for communicating with an external device.

The X-ray radiator 110 may include an X-ray source for generating X-rays and a collimator for adjusting a region irradiated with the X-rays generated by the X-ray source.

When the X-ray apparatus 100 is implemented as a mobile X-ray apparatus, a main body 101 connected to the X-ray radiator 110 is freely movable, and an arm 103 connecting the X-ray radiator 110 and the main body 101 to each other is rotatable and linearly movable. Thus, the X-ray radiator 110 may be moved freely in a three-dimensional (3D) space.

The input device 151 may receive commands for controlling imaging protocols, imaging conditions, imaging timing, and locations of the X-ray radiator 110. The input device 151 may include a keyboard, a mouse, a touch screen, a voice recognizer, etc.

The display 152 may display a screen for guiding a user's input, an X-ray image, a screen for displaying a state of the X-ray apparatus 100, and the like.

The controller 120 may control imaging conditions and imaging timing of the X-ray radiator 110 according to a control command input by the user and generate a medical image based on image data received from an X-ray detector 200. Furthermore, the controller 120 may control a position or orientation of the X-ray radiator 110 according to imaging protocols and a position of an object P.

The controller 120 may include a memory configured to store programs for performing the above operations of the X-ray apparatus 100 as well as operations thereof that will be described below and a processor configured to execute the stored programs. The controller 120 may include a single processor or a plurality of processors. When the controller 120 includes the plurality of processors, the plurality of processors may be integrated onto a single chip or be physically separated from one another.

A holder 105 may be formed on the main body 101 so as to accommodate the X-ray detector 200. Furthermore, a charging terminal is disposed in the holder 105 so as to charge the X-ray detector 200. In other words, the holder 105 may be used not only to accommodate but also to charge the X-ray detector 200.

The input device 151, the display 152, the controller 120, and the communication unit 140 may be provided on the main body 101. Image data acquired by the X-ray detector 200 may be transmitted to the main body 101 for image processing, and then the resulting image may be displayed on the display 152 or transmitted to an external device via the communication unit 140.

Furthermore, the controller 120 and the communication unit 140 may be separate from the main body 101, or only some components of the controller 120 and the communication unit 140 may be provided on the main body 101.

The X-ray apparatus 100 may be connected to external devices such as an external server 31, a medical apparatus 32, and a portable terminal 33 (e.g., a smart phone, a tablet PC, or a wearable device) in order to transmit or receive data via the communication unit 140.

The communication unit 140 may include at least one component that enables communication with an external device. For example, the communication unit 140 may include at least one of a local area communication module, a wired communication module, and a wireless communication module.

Furthermore, the communication unit 140 may receive a control signal from an external device and transmit the received control signal to the controller 120 so that the controller 120 may control the X-ray apparatus 100 according to the received control signal.

Alternatively, by transmitting a control signal to an external device via the communication unit 140, the controller 120 may control the external device according to the transmitted control signal. For example, the external device may process data according to a control signal received from the controller 120 via the communication unit 140.

Furthermore, the communication unit 140 may further include an internal communication module that enables communications between components of the X-ray apparatus 100. A program for controlling the X-ray apparatus 100 may be installed on the external device and may include instructions for performing some or all of the operations of the controller 120.

The program may be preinstalled on the portable terminal 33, or a user of the portable terminal 33 may download the program from a server providing an application for installation. The server for providing an application may include a recording medium having the program recorded thereon.

Figure 2:
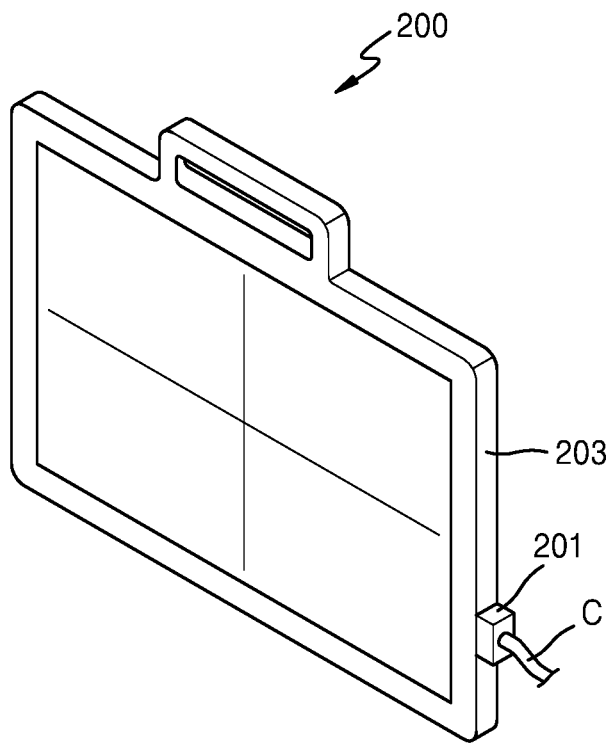
FIG. 2 is an external view of an X-ray detector included in the X-ray apparatus of FIG. 1.

FIG. 2 is an external view of the X-ray detector 200.

As described above, the X-ray detector 200 used in the mobile X-ray apparatus 100 may be implemented as a portable X-ray detector. In this case, the X-ray detector 200 may be equipped with a battery for supplying power to operate wirelessly, or as shown in FIG. 2, may operate by connecting a charge port 201 to a separate power supply via a cable C.

A case 203 maintains an external appearance of the X-ray detector 200 and has therein a plurality of detecting elements for detecting X-rays and converting the X-rays into image data, a memory for temporarily or permanently storing the image data, a communication module for receiving a control signal from the mobile X-ray apparatus 100 or transmitting the image data to the X-ray apparatus 100, and a battery. Furthermore, image correction information and intrinsic identification (ID) information of the X-ray detector 200 may be stored in the memory, and the stored ID information may be transmitted together with the image data during communication with the mobile X-ray apparatus 100.

Figure 3:
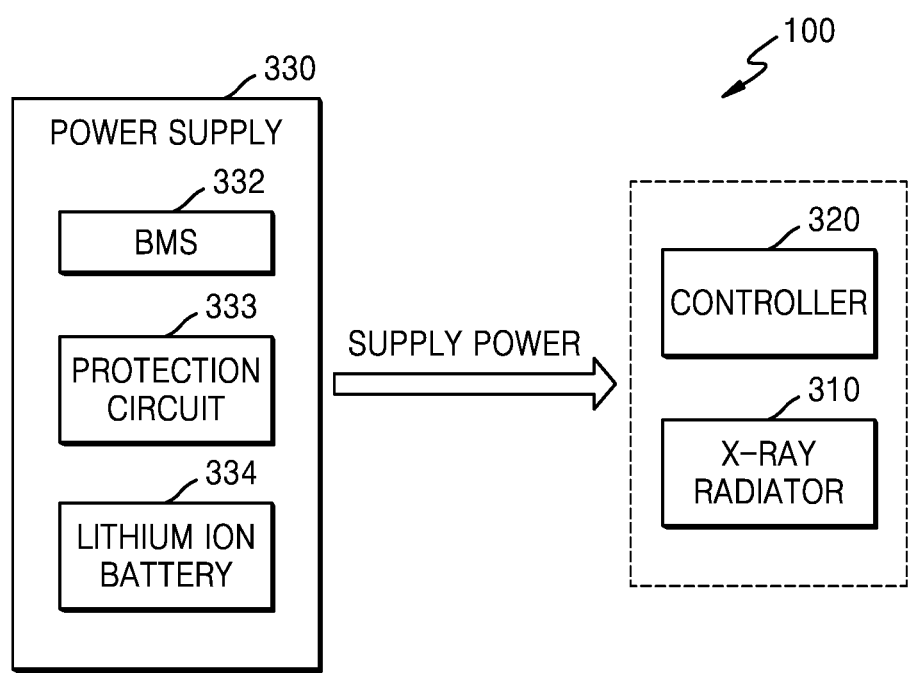
FIG. 3 is a block diagram of an X-ray apparatus according to an embodiment.

FIG. 3 is a block diagram of an X-ray apparatus 100 according to an embodiment.

Referring to FIG. 3, the X-ray apparatus 100 according to the present embodiment may include an X-ray radiator 310, a controller 320, and a power supply 330. The X-ray apparatus 100 of FIG. 3 may be implemented as a mobile X-ray apparatus as shown in FIG. 1, and FIG. 3 illustrates only components related to the present embodiment. Thus, it will be understood by those of ordinary skill in the art that the X-ray apparatus 100 may further include common components other than those shown in FIG. 3. For example, the X-ray apparatus 100 may further include a high voltage generator (not shown).

The descriptions with respect to the X-ray radiator 110 in FIG. 1 may apply to descriptions with respect to the X-ray radiator 310, and thus, are not repeated. Furthermore, the descriptions with respect to the controller 120 in FIG. 1 may apply to descriptions with respect to the controller 320, and thus, are not repeated.

The power supply 330 may include a lithium ion battery 334 and a battery management system (BMS) 332.

The lithium ion battery 334 is a type of secondary battery and consists of three components: an anode, a cathode, and an electrolyte. For example, lithium cobalt oxide ($LiCoO_2$) or lithium iron phosphate ($LiFePO_4$) may be used for the anode, and graphite may be used for the cathode. The lithium ion battery 334 may include a combination of a plurality of battery cells connected to each other. For example, the lithium ion battery 334 may include a total of three hundred fifty-two (352) cells, i.e., a serial connection of 88 cells and a parallel connection of 4 cells.

Furthermore, the lithium ion battery 334 may be suitable for use in a mobile X-ray apparatus due to its smaller size and lighter weight than conventional lead-acid batteries. For example, since a total weight of the power supply 330 including the lithium ion battery 334 and a peripheral circuit may be 33.2 kg, the total weight may be less than 35 kg, which is the maximum allowable gross weight for carrying on an aircraft. Thus, the power supply 330 may be transported by air as a single component.

The power supply 330 may supply operating power to the X-ray radiator 310 and the controller 320 via the lithium ion battery 334. Furthermore, the power supply 330 may supply operating power to components of the X-ray apparatus 100 that require the operating power. For example, the power supply 330 may supply operating power to the input device 151, the display 152, and the communication unit 140 of the X-ray apparatus 100 via the lithium ion battery 334.

The BMS 332 may detect a state of the lithium ion battery 334, such as a voltage and a temperature thereof. According to an embodiment, the BMS 332 may include a battery stack monitor circuit designed to monitor a voltage of the lithium ion battery 334 and a temperature of a battery cell. The BMS 332 may control and manage the power supply 330 based on the state of the lithium ion battery 334. Furthermore, the BMS 332 may operate a protection circuit for protecting the lithium ion battery 334 based on the state of the lithium ion battery 334. In other words, the BMS 332 may operate, based on the state of the lithium ion battery 334, the protection circuit to protect the lithium ion battery 334 from dangerous conditions. In detail, based on the state of the lithium ion battery 334, the BMS 332 may operate the protection circuit to protect the lithium ion battery 334 against at least one of over-discharge, overcurrent, overheating, and unbalancing between battery cells.

The BMS 332 may operate the protection circuit when the lithium ion battery 334 is in an over-discharged state where a voltage of the lithium ion battery 334 is lower than a reference voltage. For example, if a voltage of the lithium ion battery 334 drops to less than or equal to 275 V, the BMS 332 may operate a shutdown circuit as the protection circuit to turn itself off. In an embodiment, when an over-discharged state of the lithium ion battery 334 lasts for a preset time, the BMS 332 may transit to an over-discharge protection mode. For example, when an over-discharged state where a voltage of the lithium ion battery 334 drops to less than or equal to 275V lasts for a first time, e.g., ten (10) seconds or more, the BMS 332 may operate a shutdown circuit that is the protection circuit. Furthermore, when the over-discharged state lasts for a second time, e.g., fifty (50) seconds or more after a time point at which the BMS 332 transits to the over-discharge protection mode, the BMS 332 may be turned off by itself. According to an embodiment, the second time which it takes for the BMS 332 to turn itself off may be longer than the first time.

Furthermore, the BMS 332 may operate the protection circuit when the lithium ion battery 334 is in an overcurrent state where a charge or discharge current of the lithium ion battery 334 is higher than a reference value. For example, if the current of the lithium ion battery 334 is greater than or equal to a predetermined value, e. g., 40 A, the BMS 332 may operate a shutdown circuit as the protection circuit to turn itself off. The BMS 332 may also operate the protection circuit when the lithium ion battery 334 is in an overheated state where a temperature of the lithium ion battery 334 is higher than a reference value. For example, if the temperature of the lithium ion battery 334 is greater than or equal to 70° C., the BMS 332 may operate the shutdown circuit to turn itself off. Furthermore, when the lithium ion battery 334 is unbalanced between battery cells, the BMS 332 may operate the protection circuit. For example, if a voltage difference between cells in the lithium ion battery 334 remains greater than or equal to 0.5 V for ten (10) seconds or more, the BMS 332 may operate a shutdown circuit to turn itself off. For example, if a voltage difference between a maximum voltage and a minimum voltage among voltages of cells in the lithium ion battery 334 remains greater than or equal to 0.5 V for ten (10) seconds or more, the BMS 332 may operate a shutdown circuit to turn itself off.

According to another embodiment, if at least one of over-discharge, overcurrent, overheating, and unbalancing between battery cells occurs based on the state of the lithium ion battery 334, the BMS 332 may cut off, before operating the protection circuit, a charge path and/or a discharge path by using a charge controller and/or a discharge controller for controlling the charge path and/or the discharge path. The charge controller may include a charge FET, and the discharge controller may include a discharge FET.

The BMS 332 may control an operation of a protection circuit during X-ray emission by the X-ray radiator 310. When the X-ray radiator 310 emits X-rays, the lithium ion battery 334 may become transiently over-discharged, enter an overcurrent state, be overheated, or become unbalanced between cells due to a momentary overcurrent, which may cause the BMS 332 to have the protection circuit unnecessarily operate. In this case, by operating the protection circuit, the X-ray emission may not occur. Thus, to prevent unnecessary operations of the protection circuit, the BMS 332 may control an operation of the protection circuit exceptionally during emission of X-rays.

According to an embodiment, when X-rays are emitted, the BMS 332 may change an overcurrent reference value and/or an over-discharge reference value for the lithium ion battery 334, which are used for operating the protection circuit. In other words, when X-rays are emitted, the BMS 332 may increase a current reference value for operating the protection circuit due to the occurrence of overcurrent, compared to an existing current reference value, and may decrease a voltage reference value for operating the protection circuit due to the occurrence of over-discharge, compared to an existing voltage reference value. Furthermore, the BMS 332 may change the overcurrent reference value and/or the over-discharge reference value based on an X-ray emission preparation signal. In detail, the BMS 332 may receive a signal indicating that the X-ray radiator 310 starts X-ray emission from the controller 320 and change the overcurrent reference value and/or the over-discharge reference value based on the received signal. Subsequently, the BMS 332 may change, based on an X-ray emission completion signal, the changed overcurrent reference value and/or the changed over-discharge reference value back to the same overcurrent and/or over-discharge reference value(s) as before. In detail, the BMS 332 may receive a signal indicating that the X-ray radiator 310 has completed the X-ray emission from the controller 320 and respectively change, based on the received signal, the changed overcurrent reference value and/or the changed over-discharge reference value back to the same overcurrent and/or over-discharge reference value(s) as before. Similarly, when X-ray emission occurs, the BMS 332 may change an overheating reference value and/or a cell unbalancing reference value for the lithium ion battery 334, which are/is used for operating the protection circuit.

According to another embodiment, when X-rays are emitted, the BMS 332 may prevent the protection circuit from operating protection against over-discharge and/or overcurrent. In detail, the BMS 332 may receive a signal indicating that the X-ray radiator 310 starts X-ray emission from the controller 320 and prevent the protection circuit from operating protection against over-discharge and/or overcurrent based on the received signal. Subsequently, the BMS 332 may receive a signal indicating that the X-ray emission is completed from the controller 320 and allow the protection circuit to operate to protect against over-discharge and/or overcurrent based on the received signal. Similarly, when the X-ray emission occurs, the BMS 332 may prevent the protection circuit from operating protection against overheating and/or unbalancing between cells.

According to another embodiment, the BMS 332 may prevent the protection circuit from protecting against over-discharge and/or overcurrent during the time when X-rays are emitted. In detail, the BMS 332 may pause an operation of the protection circuit until a lapse of a preset time period starting from a time point when an X-ray emission signal indicating that the X-ray radiator 310 starts X-ray emission is received from the controller 320. As another example, the BMS 332 may control the protection circuit to resume protection against over-discharge or overcurrent after a lapse of a preset time period starting from a time point when an X-ray emission preparation signal is received. Similarly, the BMS 332 may prevent the protection circuit from protecting against overheating and/or unbalancing between cells during the time when X-rays are emitted. In detail, the BMS 332 may pause an operation of the protection circuit against overheating and/or unbalancing between cells up until a preset time period elapses starting from a time point when an X-ray emission signal is received from the controller 320. As another example, the BMS 332 may control the protection circuit to resume protection against overheating and/or unbalancing between cells after a preset time period elapsed starting from a time point when an X-ray emission preparation signal is received from the controller 320.

The power supply 330 and the controller 320 may each include a communication interface that enables communication therebetween. For example, the power supply 330 and the controller 320 may communicate with each other via their communication interfaces according to a controller area network (CAN) protocol. Furthermore, according to another embodiment, communication between the power supply 330 and the controller 320 may be performed by using a high-speed digital interface such as low voltage differential signaling (LVDS), an asynchronous serial communication protocol such as universal asynchronous receiver transmitter (UART), a low-latency network protocol such as an error synchronous serial communication protocol, or other various communication methods that are obvious to those of ordinary skill in the art.

Furthermore, the power supply 330 and the controller 320 may each be constituted by a different module.

Figure 4:
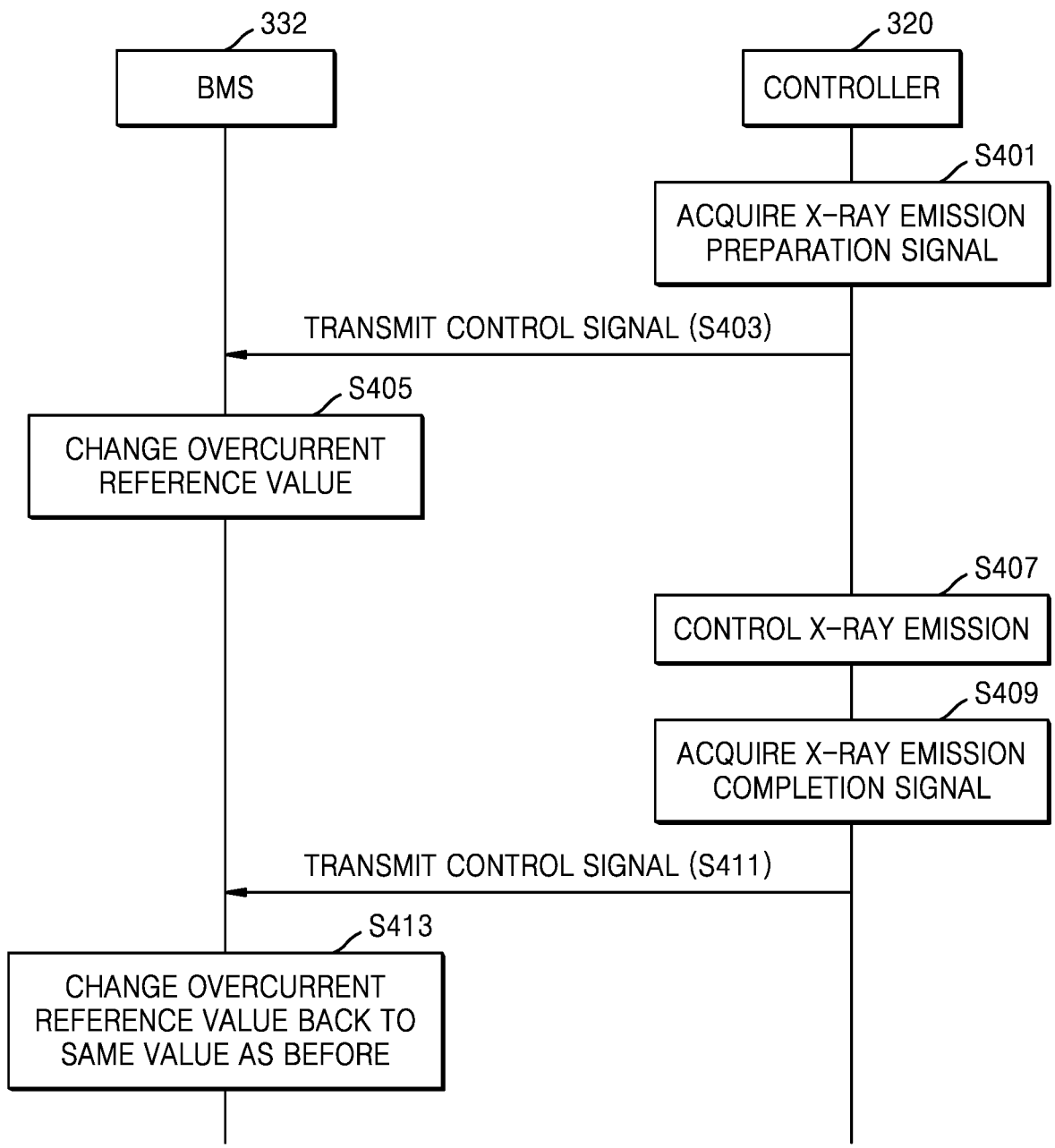
FIG. 4 is a flowchart of a method, performed by a battery management system (BMS), of controlling an operation of a protection circuit protecting against overcurrent during X-ray emission, according to an embodiment.

FIG. 4 is a flowchart of a method, performed by the BMS 332, of controlling an operation of a protection circuit protecting against overcurrent during X-ray emission, according to an embodiment.

Referring to FIG. 4, the controller 320 may acquire an X-ray emission preparation signal (S401). According to an embodiment, the controller 320 may acquire the X-ray emission preparation signal via the input device 151. For example, if the input device 151 is formed as a two-step push hand switch, the user may press a button on the two-step push hand switch, which is the input device 151, to a first step indicating an X-ray emission command, and the controller 320 may receive the X-ray emission preparation signal via pressing of the button on the input device 151 to the first step.

The controller 320 may transmit a control signal generated based on the received X-ray emission preparation signal to the BMS 332 (S403). According to an embodiment, the controller 320 may transmit the control signal generated based on the X-ray emission preparation signal to the BMS 332 via a communication interface. In other words, the controller 320 may transmit the control signal to the BMS 332 as a signal indicating preparation of X-ray emission. According to another embodiment, the BMS 332 may directly receive an X-ray emission preparation signal generated in the input device 151 as the control signal. In this case, the X-ray emission preparation signal may be transmitted to the BMS 332 without passing through the controller 320.

The BMS 332 may change an overcurrent reference value based on the received control signal (S405). According to an embodiment, the BMS 332 may increase a current reference value for operating a protection circuit due to the occurrence of overcurrent, compared to an existing current reference value. For example, the BMS 332 may change the current reference value from 40 A to 300 A or more.

The controller 320 may control the X-ray radiator 310 to emit X-rays (S407). According to an embodiment, if the user fully presses (to a second step) the button on the input device 151, which is already pressed to the first step, the controller 320 may then receive an X-ray emission signal and control the X-ray radiator 310 to emit X-rays. As the X-rays are emitted, overcurrent may occur in the lithium ion battery 334, but the BMS 332 may not operate the protection circuit based on the overcurrent reference value changed in operation S405. Thus, since the BMS 332 may prevent unnecessary operations of the protection circuit, current may flow from the lithium ion battery 334 to the X-ray radiator 310 through a high voltage generator, causing X-rays generated by the X-ray radiator 310 to be emitted towards an object.

The controller 320 may acquire an X-ray emission completion signal (S409). According to an embodiment, the controller 320 may acquire the X-ray emission completion signal from the high voltage generator or the X-ray detector 200 of the X-ray apparatus 100. Furthermore, according to another embodiment, if the user has not pressed a button on the input device 151 for a specific amount of time, or as soon as the user releases the button on the input device 151, the controller 320 may receive a signal indicating the completion of X-ray emission.

The controller 320 may transmit a control signal generated based on the received X-ray emission completion signal to the BMS 332 (S411). According to an embodiment, the controller 320 may transmit the control signal generated based on the X-ray emission completion signal to the BMS 332 via the communication interface.

The BMS 332 may respectively change, based on the received control signal, the changed overcurrent reference value back to the same overcurrent reference value as before (S413). In other words, in order to exceptionally operate the protection circuit only during the X-ray emission, if the X-ray emission is completed, the BMS 332 may set the overcurrent reference value to the same value as before. Thus, by changing the overcurrent reference value in this way, the BMS 332 may prevent the protection circuit from operating even when overcurrent flows in the lithium ion battery 334 during X-ray emission because a current value falls below the overcurrent reference value. Accordingly, X-rays may be emitted by the X-ray radiator 310.

According to another embodiment, without receiving the control signal transmitted in operation S411, the BMS 332 may change the changed overcurrent reference value back to the same overcurrent reference value as before after a preset time (e.g., 10 seconds) has lapsed.

According to another embodiment, the BMS 332 may prevent the protection circuit from operating protection against overcurrent without changing the overcurrent reference value in operation S405. In this case, even when X-rays are emitted in operation S407, the BMS 332 is not turned off. Thereafter, when the control signal generated based on the X-ray emission completion signal is received in operation S411, the BMS 332 may control the protection circuit for protecting against overcurrent to operate again in operation S413.

Figure 5:
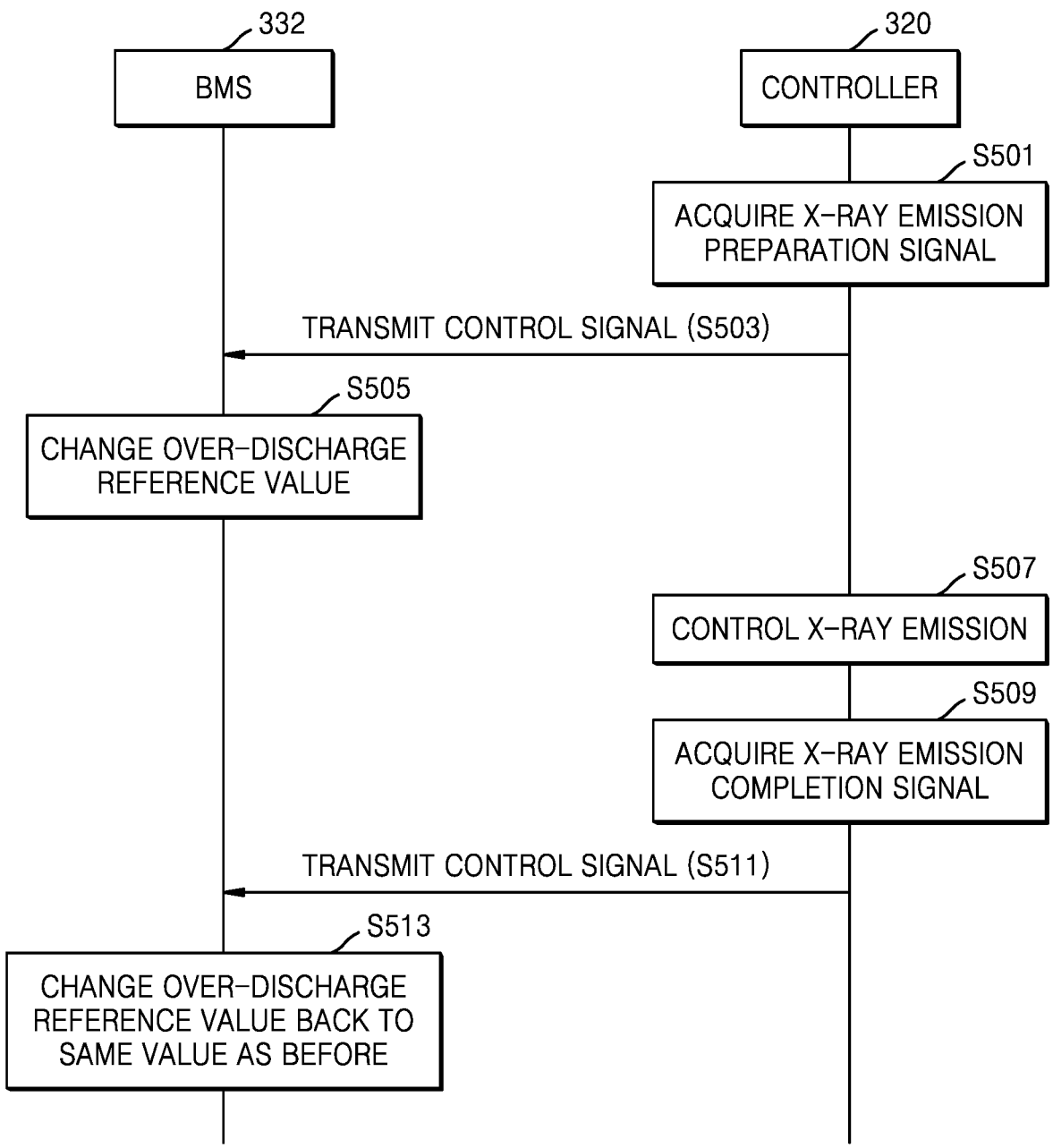
FIG. 5 is a flowchart of a method, performed by a BMS, of controlling an operation of a protection circuit protecting against over-discharge during X-ray emission, according to an embodiment.

FIG. 5 is a flowchart of a method, performed by the BMS 332, of controlling an operation of a protection circuit protecting against over-discharge (overvoltage) during X-ray emission, according to an embodiment.]

Referring to FIG. 5, the controller 320 may acquire an X-ray emission preparation signal (S501).

The controller 320 may transmit a control signal generated based on the acquired X-ray emission preparation signal to the BMS 332 (S503).

The BMS 332 may change an over-discharge reference value based on the received control signal (S505). According to an embodiment, the BMS 332 may decrease a voltage reference value for operating a protection circuit due to the occurrence of over-discharge, compared to an existing current reference value. For example, the BMS 332 may change the voltage reference value from 275V to 200V or less.

The controller 320 may control the X-ray radiator 310 to emit X-rays (S507). As the X-rays are emitted, over-discharge may occur in the lithium ion battery 334, but the BMS 332 may not operate the protection circuit based on the over-discharge reference value changed in operation S505. Thus, the BMS 332 may prevent unnecessary operations of the protection circuit.

The controller 320 may acquire an X-ray emission completion signal (S509). According to an embodiment, the controller 320 may receive the X-ray emission completion signal from the high voltage generator or the X-ray detector 200. According to another embodiment, the BMS 332 may directly receive an X-ray emission preparation signal generated in the input device 151 as a control signal. In this case, the X-ray emission preparation signal may be transmitted to the BMS 332 without passing through the controller 320.

The controller 320 may transmit a control signal generated based on the acquired X-ray emission completion signal to the BMS 332 (S511).

The BMS 332 may change, based on the received control signal, the changed over-discharge reference value back to the same over-discharge reference value as before (S513). In other words, in order to exceptionally operate the protection circuit only during the X-ray emission, if the X-ray emission is completed, the BMS 332 may set the over-discharge reference value to the same value as before.

According to another embodiment, without receiving the control signal transmitted in operation S511, the BMS 332 may change the changed over-discharge reference value back to the same over-discharge reference value as before after a preset time (e.g., 10 seconds) has lapsed.

According to another embodiment, the BMS 332 may prevent the protection circuit from operating protection against over-discharge (overvoltage) without changing the over-discharge reference value in operation S505. Thus, even when X-rays are emitted in operation S507, the BMS 332 is not turned off. Thereafter, when receiving the control signal generated based on the X-ray emission completion signal in operation S511, the BMS 332 may control the protection circuit for protecting against over-discharge (overvoltage) to operate again in operation S513.

While it has been described that the BMS 332 controls operations of a protection circuit protecting against overcurrent and over-discharge, the BMS 332 may also control operations of the protection circuit protecting against overheating and/or unbalancing between cells in the same manner as described with reference to FIGS. 4 and 5.

According to another embodiment, after receiving a control signal generated based on an X-ray emission preparation signal from the controller 320, the BMS 332 may prevent the protection circuit from operating based on the received control signal. In other words, even when at least one of overcurrent, over-discharge, overcurrent, overheating, and unbalancing between cells is received from a sensor during X-ray emission, the BMS 332 does not generate a signal that causes the protection circuit to operate.

Figure 6:
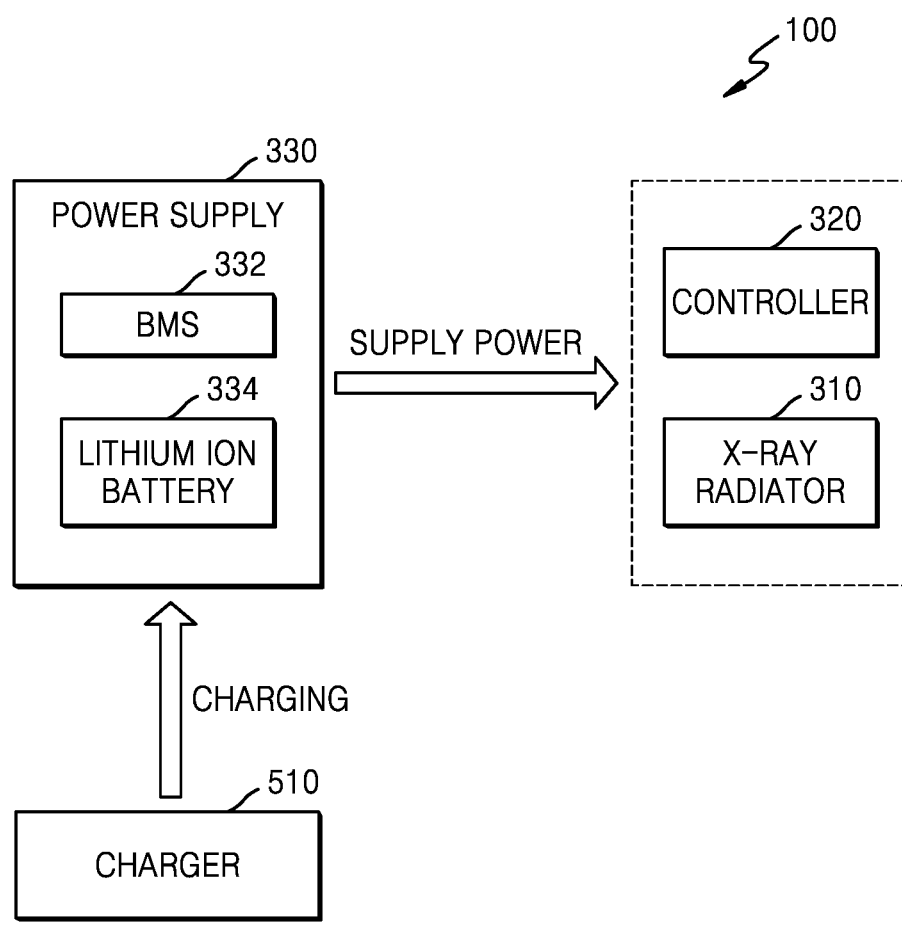
FIG. 6 is a block diagram of an X-ray apparatus according to an embodiment.

FIG. 6 is block diagram of an X-ray apparatus 100 according to an embodiment.

Unlike the X-ray apparatus 100 of FIG. 3, the X-ray apparatus 100 of FIG. 6 may further include a charger 510.

The charger 510 may charge the power supply 330. In detail, the charger 510 may supply a charging power to charge the lithium ion battery 334 of the power supply 330. In this case, the charging power may be a power generated by the charger 510. According to an embodiment, the charger 510 may be combined with an external power supply to receive power from the external power supply. The charger 510 may then control the received power according to a user input or arithmetic operations performed within the X-ray apparatus 100 to supply a charging power to the lithium ion battery 334.

The charger 510 may control a charging operation during X-ray emission by the X-ray radiator 310. The charger 510 may stop the charging operation when the X-ray radiator 310 emits X-rays. When the X-rays are emitted while the charger 510 is being connected to the power supply 330 to perform the charging operation, the charger 410 may be damaged by momentary overloads. Thus, to prevent the damage to the charger 510 due to momentary overloads, the charger 510 may stop the charging operation exceptionally when the X-ray radiator 310 emits the X-rays. When the X-ray emission is completed, the charger 510 may resume the charging operation.

The power supply 330, the charger 510, and the controller 320 may each include a communication interface that enables communication therebetween. For example, the power supply 330, the charger 510, and the controller 320 may communicate with one another via their communication interfaces according to a CAN protocol. Furthermore, according to another embodiment, communications may be performed among the power supply 330, the charger 510, and the controller 320 by using a high-speed digital interface such as LVDS, an asynchronous serial communication protocol such as UART, a low-latency network protocol such as an error synchronous serial communication protocol, or other various communication methods that are obvious to those of ordinary skill in the art.

Furthermore, the power supply 330, the charger 510, and the controller 320 may each be constituted by a different module. Thus, since the controller 320 does not need to directly monitor a high voltage, a high voltage circuit is not needed within the controller 320. This may consequently reduce the risks associated with the high voltage circuit, thereby effectively improving stability.

In detail, in a mobile X-ray apparatus using a conventional lead-acid battery, a controller may include a circuit for monitoring a high voltage state, and may be damaged by high voltages. On the other hand, in the X-ray apparatus 100 according to the present embodiment, a BMS of the power supply 330 may monitor a high voltage state and transmit the high voltage state to the controller 320. This configuration may reduce the risk of damage to the controller 320.

Furthermore, when the power supply 330, the charger 510, and the controller 320 are each constituted by a different module, they may be used for different mobile X-ray apparatuses and thus share a common platform. Furthermore, by applying a shield case to each of the power supply 330, the charger 510, and the controller 320 that are respectively constituted by different modules, it is possible to suppress Electro Magnetic Interference (EMI)/Electro Magnetic Compatibility (EMC) noise that may occur therebetween.

Figure 7:
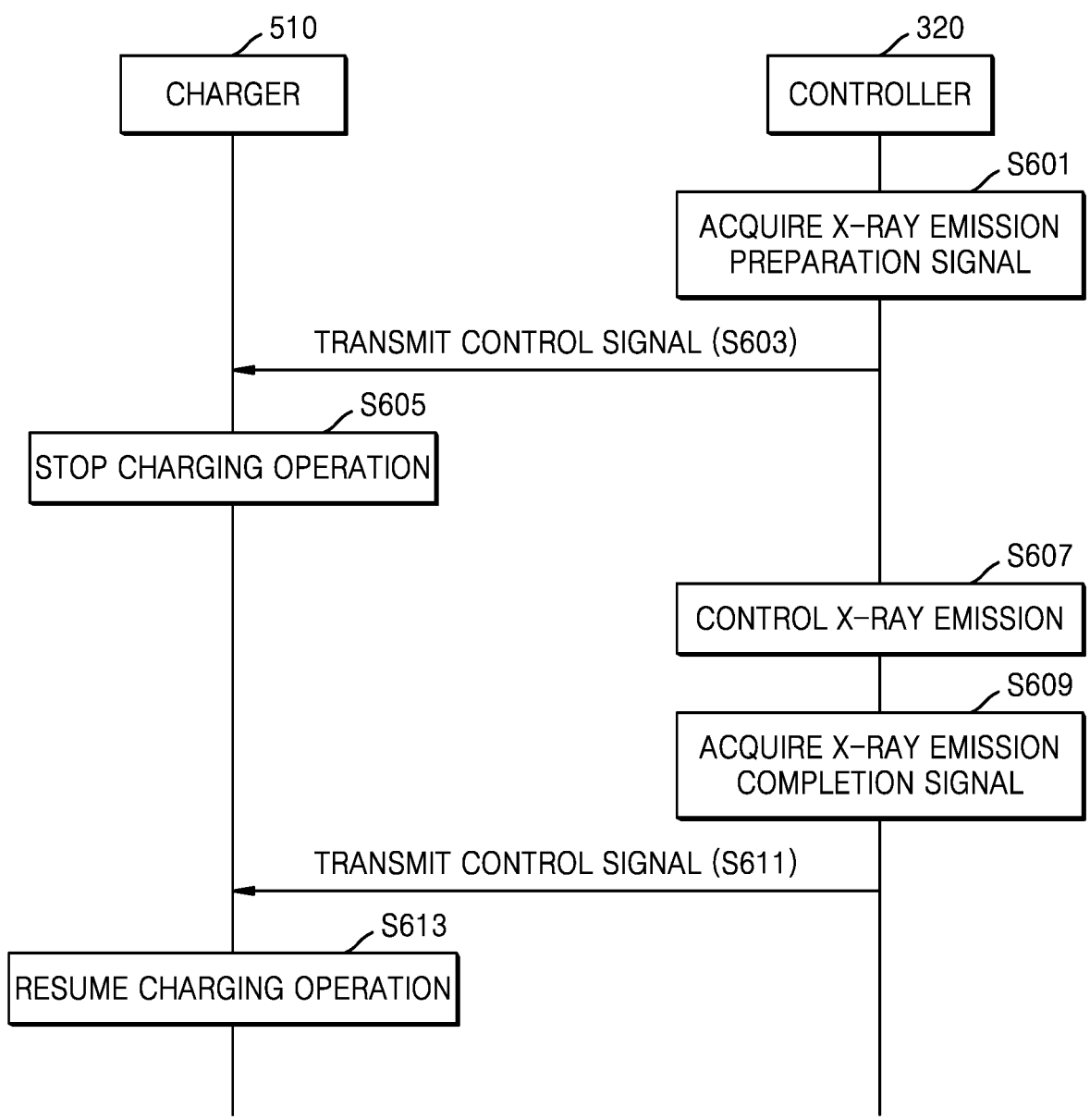
FIG. 7 is a flowchart of a method, performed by a charger, of controlling a charging operation during X-ray emission, according to an embodiment.

FIG. 7 is a flowchart of a method, performed by the charger 510, of controlling a charging operation during X-ray emission, according to an embodiment.

Referring to FIG. 7, the controller 320 may acquire an X-ray emission preparation signal (S601). According to an embodiment, the controller 320 may acquire the X-ray emission preparation signal via the input device 151. For example, if the input device 151 is implemented as a hand switch, the user may partially press a button on the input device 151 indicating an X-ray emission command, and the controller 320 may acquire the X-ray emission preparation signal via the partially pressed button on the input device 151.

The controller 320 may transmit a control signal generated based on the acquired X-ray emission preparation signal to the charger 510 (S603). According to an embodiment, the controller 320 may transmit the control signal generated based on the X-ray emission preparation signal to the charger 510 via a communication interface.

According to another embodiment, the charger 510 may directly receive an X-ray emission preparation signal generated in the input device 151 as the control signal. In this case, the X-ray emission preparation signal may be transmitted to the charger 510 without passing through the controller 320.

The charger 510 may stop charging of the power supply 330 based on the received control signal (S605).

The controller 320 may control the X-ray radiator 310 to emit X-rays (S607). According to an embodiment, if the user fully presses an already partially pressed button on the input device 151, the controller 320 may then control the X-ray radiator 310 to emit X-rays. As the X-rays are emitted and the charger 510 stops the charging, the charger 510 may not be damaged by momentary overloads.

The controller 320 may acquire an X-ray emission completion signal (S609). According to an embodiment, the controller 320 may acquire the X-ray emission completion signal from the high voltage generator or the X-ray detector 200 of the X-ray apparatus 100. Furthermore, according to another embodiment, if the user has not pressed a button on the input device 151 for a specific amount of time, the controller 320 may acquire a signal indicating the completion of X-ray emission.

The controller 320 may transmit a control signal generated based on the acquired X-ray emission completion signal to the charger 510 (S611). According to an embodiment, the controller 320 may transmit the control signal to the charger 510 via the communication interface, and the charger 510 may receive the control signal.

The charger 510 may resume the stopped charging based on the received control signal (S613). In other words, the charger 510 may stop the charging exceptionally only when the X-rays are emitted.

According to another embodiment, without receiving the control signal transmitted in operation S611, the charger 510 may resume the charging after a preset time (e.g., 10 seconds) has lapsed.

Figure 8:
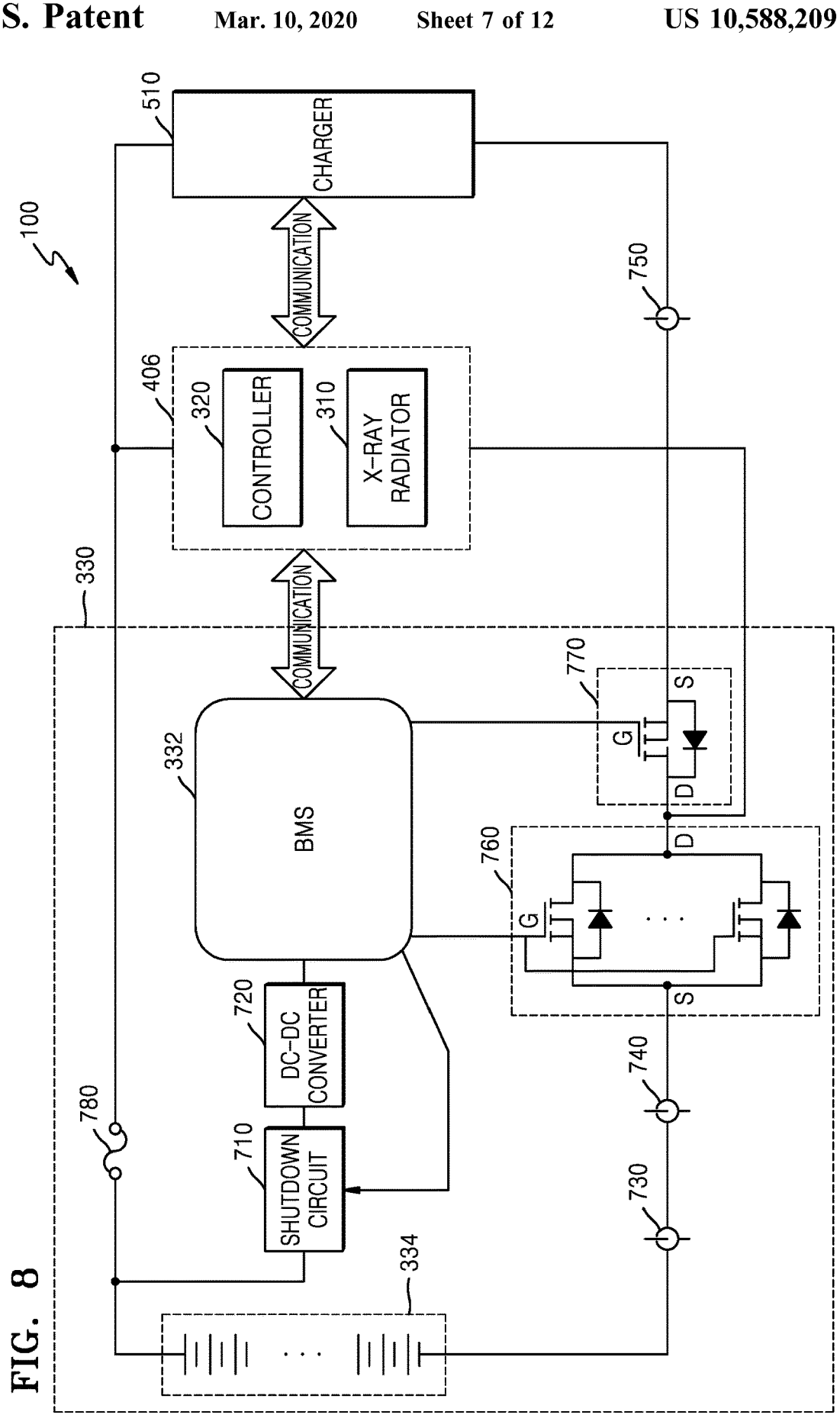
FIG. 8 illustrates an X-ray apparatus according to an embodiment.

FIG. 8 illustrates an X-ray apparatus 100 according to an embodiment.

Referring to FIG. 8, a power supply 330 may include a lithium ion battery 334, the BMS 332, a discharge FET 760, a charge FET 770, a shutdown circuit 710, the first current sensor 730, the second current sensor 740, a direct current (DC)-to-DC (DC-DC) converter 720, and a fuse 780. Furthermore, the X-ray apparatus 100 may include a third current sensor 750.

The first and second current sensors 730 and 740 may include a Hall sensor, and the shutdown circuit 710 that is a protection circuit may include a switching circuit such as a FET.

The BMS 332 may control a charge path and a discharge path by using the charge FET 770 that is a charge controller and the discharge FET 760 that is a discharge controller. In other words, the BMS 332 may control the charge path and the discharge path by controlling on/off states of the charge FET 770 and the discharge FET 760.

The BMS 332 may also communicate with a controller 320 via a communication interface to monitor a state of the power supply 330.

The discharge FET 760 may include a plurality of FETs connected in parallel. Since overcurrent may flow in the power supply 330 during X-ray emission by the X-ray radiator 310, the FETs having a specific capacity in the discharge FET 760 may be connected in parallel. For example, if overcurrent greater than or equal to 300 A flows within the power supply 330 during X-ray emission by the X-ray radiator 310, the discharge FET 760 may be constituted by four (4) parallel connected FETs having a capacity of 100 A for protection against the overcurrent.

According to an embodiment, the discharge FET 760 and the charge FET 770 may each be constituted by an N-channel FET.

The discharge FET 760 and the charge FET 770 may control a path of discharge or charge current when the lithium ion battery 334 is discharged or charged. According to an embodiment, when the lithium ion battery 334 is discharged, the charge FET 770 may be turned off, and a discharge current loop may be formed by the discharge FET 760 that is in an on-state. According to another embodiment, when the lithium ion battery 334 is charged, the discharge FET 760 may be turned off, and a charge current loop may be formed by a body diode of the discharge FET 760 and the charge FET 770 that is in the on-state. Furthermore, the lithium ion battery 334 may be discharged and charged at the same time via the discharge FET 760 and the charge FET 770.

According to another embodiment, the BMS 332 may sequentially perform discharging and charging by sequentially controlling the discharge FET 760 and the charge FET 770.

The BMS 332 may detect a current of the lithium ion battery 334 by using different current sensors, i.e., the first and second current sensors 730 and 740. In detail, the BMS 332 may detect a current flowing in the lithium ion battery 334 by using the first current sensor 730. The first current sensor 730 may be a small-capacity sensor for detecting a current having a relatively low intensity. In other words, the first current sensor 730 may be a sensor for detecting a current having an intensity less than or equal to a reference level. For example, the first current sensor 730 may detect a current that is less than or equal to 50 A. Furthermore, when overcurrent flows in the lithium ion battery 334, the BMS 332 may detect overcurrent flowing in the lithium ion battery 334 by using the second current sensor 740 since it is difficult to accurately detect the overcurrent via the first current sensor 730. The second current sensor 740 may be a large-capacity sensor for detecting a current having a relatively high intensity. In other words, the second current sensor 740 may be a sensor for detecting a current having an intensity greater than or equal to a reference level. For example, the second current sensor 740 may detect a current that is greater than or equal to 300 A. Thus, the first and second current sensors 730 and 740 may be configured to detect different levels of current. For example, the second current sensor 740 may detect a higher level of current than the first current sensor 730.

According to an embodiment, the BMS 332 may detect, via the first current sensor 730, current flowing in the lithium ion battery 334 by activating the first current sensor 730 while deactivating the second current sensor 740. Then, when an X-ray radiator 310 emits X-rays, the BMS 332 may detect overcurrent that occurs during the X-ray emission via the second current sensor 740 by activating the second current sensor 740 while deactivating the first current sensor 730. Subsequently, when the X-ray emission is completed, the BMS 332 may detect, via the first current sensor 730, current flowing in the lithium ion battery 334 by activating the first current sensor 730 while deactivating the second current sensor 740.

According to another embodiment, when the X-ray radiator 310 emits X-rays, the BMS 332 may detect overcurrent by activating the second current sensor 740. The BMS 332 may also activate the first current sensor 730 but ignore a signal received from the first current sensor 730. After completion of the X-ray emission, the second current sensor 740 may be deactivated. As another example, the second current sensor 740 may remain activated, but the BMS 332 may ignore a signal received from the second current sensor 740.

According to another embodiment, the first and second current sensors 730 and 740 remain in the on-state regardless of whether the X-ray emission occurs. In this case, the BMS 332 may selectively use signals received from the first and second current sensors 730 and 740 according to whether the X-ray emission occurs. For example, before receiving a signal related to X-ray emission preparation and after a signal related to X-ray emission completion, the BMS 332 may control the power supply 330 based on a signal received from the first current sensor 730. Furthermore, before receiving the signal related to X-ray emission completion after receiving the signal related to X-ray emission preparation, the BMS 332 may control the power supply 330 based on a signal received from the second current sensor 740.

The BMS 332 may check the residual amount of the lithium ion battery 334 based on the amount of current detected using different current sensors, i.e., the first and second current sensors 730 and 740. In detail, the BMS 332 may use Coulomb Counting Based Gauging to check the residual amount of the lithium ion battery 334 based on the detected amount of current.

Furthermore, the X-ray apparatus 100 may further include the third current sensor 750 for measuring a charge current. In other words, the X-ray apparatus 100 may further include the third current sensor 750 at an output terminal of the charger 510. When the lithium ion battery 334 is charged and discharged at the same time, current measured by the first and second current sensors 730 or 740 may be a sum of a discharge current and a charge current. Thus, in order to accurately measure a discharge current and a charge current, the X-ray apparatus 100 may measure the charge current by using the third current sensor 750.

The BMS 332 may turn itself off by using the shutdown circuit 710. When the BMS 332 may check a state of the lithium ion battery 334 to detect hazardous conditions such as over-discharge and overcharge, the BMS 332 may turn itself off by using the shutdown circuit 710 that serves as a protection circuit. When the BMS 332 is turned off, the charge controller and the discharge controller may be turned off to prevent power from being supplied via a charge path and a discharge path. Furthermore, power being supplied to the controller 320 is also cut off, so that the controller 320 may turn off.

The fuse 780 is designed to stop continuous flowing of excessive current that is greater than a nominal value in the power supply 330 and may protect a battery cell when the lithium ion battery 334 is subjected to an external short circuit.

The DC-DC converter 720 may convert a voltage of the lithium ion battery 334 into a DC power for operating the BMS 332.

Furthermore, while FIG. 8 shows that a load 406 for receiving a power from the lithium ion battery 334 via a charge path and/or a discharge path includes the controller 320 and the X-ray radiator 310, the load 406 may further include other components of the X-ray apparatus 100 that require power. For example, the load 406 may include a high voltage generator, a motor driver for moving the X0ray apparatus 100, etc.

Figure 9:
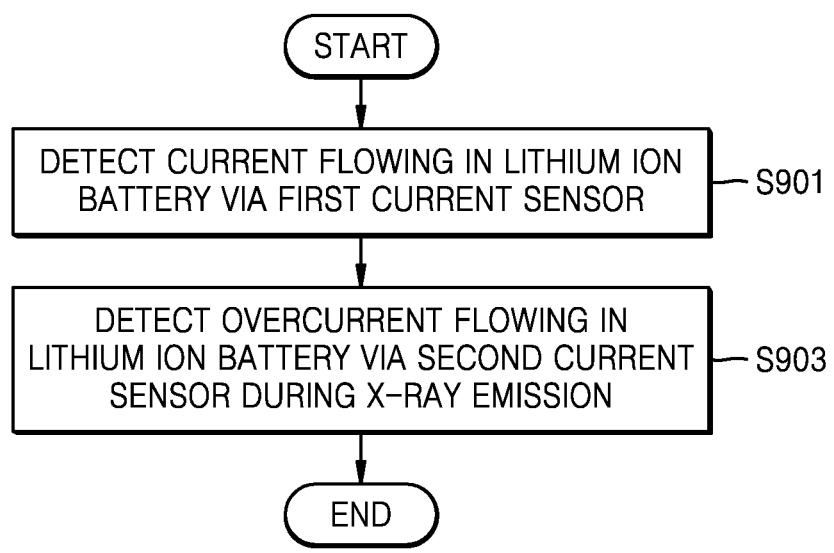
FIG. 9 is a flowchart of a method, performed by an X-ray apparatus, of detecting a current flowing in a lithium ion battery via a current sensor, according to an embodiment.

FIG. 9 is a flowchart of a method, performed by the X-ray apparatus (100 of FIG. 8), of detecting a current flowing in the lithium ion battery 334 via a current sensor, according to an embodiment.

Referring to FIG. 9, the X-ray apparatus 100 may detect the current flowing in the lithium ion battery 334 via the first current sensor 730 (S901). By activating the first current sensor 730, the X-ray apparatus 100 may detect the current flowing in the lithium ion battery 334 via the activated first current sensor 730. Under normal conditions, the X-ray apparatus 100 may detect the current flowing in the lithium ion battery 334 via the first current sensor 730. A value of the detected current may be transmitted to the BMS 332.

During X-ray emission, the X-ray apparatus 100 may detect overcurrent flowing in the lithium ion battery 334 via the second current sensor 740 (S903). In this case, by activating the second current sensor 740, the X-ray apparatus 100 may detect the overcurrent flowing in the lithium ion battery 334 via the activated second current sensor 740. The X-ray apparatus 100 may detect, under normal conditions, current flowing in the lithium ion battery 334 via the first current sensor 730, and sense, during the X-ray emission, the overcurrent flowing in the lithium ion battery 334 via the second current sensor 740.

Figure 10:
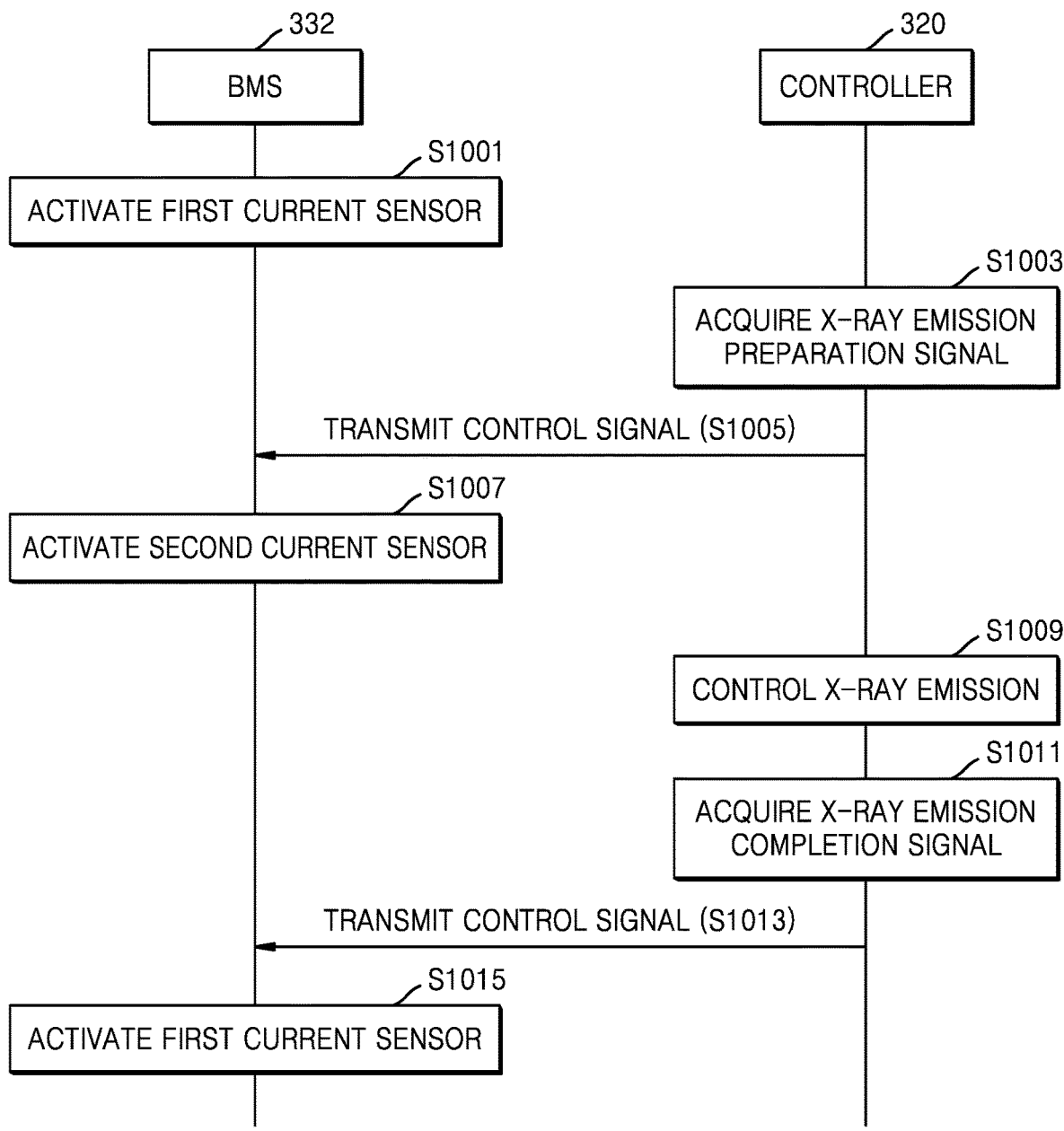
FIG. 10 is a flowchart of a method, performed by a BMS, of controlling a first current sensor and a second current sensor during X-ray emission, according to an embodiment.

FIG. 10 is a flowchart of a method, performed by the BMS 332, of controlling the first current sensor 730 and the second current sensor 740 during X-ray emission, according to an embodiment.

Referring to FIG. 10, the BMS 332 may activate the first current sensor 730 (S1001). In this case, the BMS 332 may be prevented from receiving a signal from the second current sensor 740 by deactivating the second current sensor 740 together with activation of the first current sensor 730. Thus, the BMS 332 may detect a current flowing in the lithium ion battery 334 by using the first current sensor 730.

According to another embodiment, when the second current sensor 740 remains activated, the BMS 332 may not use a signal received from the second current sensor 740 for control of the power supply 330 or ignore the received signal.

The controller 320 may acquire an X-ray emission preparation signal (S1003). According to an embodiment, the controller 320 may acquire the X-ray emission preparation signal from the high voltage generator or the X-ray detector 200 or via the input device 151. For example, if the input device 151 is implemented as a hand switch, the user may partially press a button on the input device 151 indicating an X-ray emission command, and the controller 320 may acquire the X-ray emission preparation signal via the partially pressed button on the input device 151.

The controller 320 may transmit a control signal generated based on the acquired X-ray emission preparation signal to the BMS 332 (S1005). According to an embodiment, the controller 320 may transmit the control signal generated based on the X-ray emission preparation signal to the BMS 332 via a communication interface.

The BMS 332 may activate the second current sensor 740 based on the received control signal (S1007). In this case, the BMS 332 may be prevented from receiving a signal from the first current sensor 730 by deactivating the first current sensor 730.

According to another embodiment, when the first current sensor 730 remains activated, the BMS 332 may not use a signal received from the first current sensor 730 for control of the power supply 330 or ignore the received signal.

The controller 320 may control the X-ray radiator 310 to emit X-rays (S1009). According to an embodiment, if the user fully presses an already partially pressed button on the input device 151, the controller 320 may then control the X-ray radiator 310 to emit X-rays. As the X-rays are emitted, overcurrent may occur in the lithium ion battery 334, and the BMS 332 may detect a current flowing in the lithium ion battery 334 via the activated second current sensor 740.

The controller 320 may acquire an X-ray emission completion signal (S1011). According to an embodiment, the controller 320 may acquire the X-ray emission completion signal from the high voltage generator or the X-ray detector 200 of the X-ray apparatus 100. Furthermore, according to another embodiment, if the user has not pressed a button on the input device 151 for a specific amount of time, the controller 320 may acquire a signal indicating the completion of X-ray emission.

The controller 320 may transmit a control signal generated based on the acquired X-ray emission completion signal to the BMS 332 (S1013). According to an embodiment, the controller 320 may transmit the control signal generated based on the X-ray emission completion signal to the BMS 332 via the communication interface.

The BMS 332 may activate the first current sensor 730 based on the received control signal (S1015). In this case, the BMS 332 may deactivate the second current sensor 740 together with activation of the first current sensor 730. In other words, the BMS 332 may detect overcurrent by activating the second current sensor 740 exceptionally only when the X-rays are emitted.

According to another embodiment, when the second current sensor 740 remains activated, the BMS 332 may not use a signal received from the second current sensor 740 for control of the power supply 330 or ignore the received signal.

Figure 11:
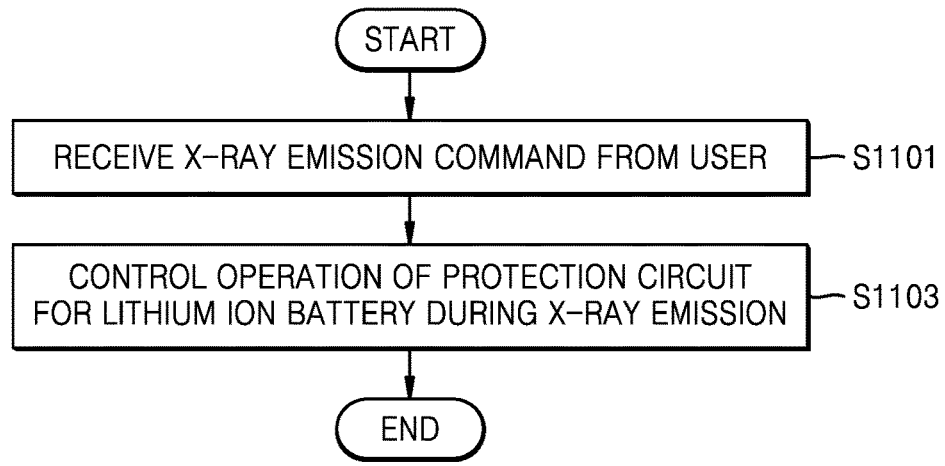
FIG. 11 is a flowchart of a method of operating an X-ray apparatus, according to an embodiment.

FIG. 11 is a flowchart of a method of operating an X-ray apparatus, according to an embodiment.

The method illustrated in FIG. 10 may be performed by components of the X-ray apparatuses 100 of FIGS. 1, 3, 6, and 8, and descriptions that are already provided with respect to FIGS. 1, 3, 6, and 8 will be omitted below.

Referring to FIG. 11, the X-ray apparatus 100 may receive an X-ray emission command from a user (S1101). According to an embodiment, the X-ray apparatus 100 may receive the X-ray emission command from the user via the input device 151 of the X-ray apparatus 100. For example, if the input device 151 is implemented as a hand switch, the user may press a button on the input device 151 indicating the X-ray emission command, and the X-ray apparatus 100 may receive the X-ray emission command from the user via the pressed button. Furthermore, according to an embodiment, the user may partially press the button on the input device 151 indicating the X-ray emission command, and the X-ray apparatus 100 may receive an X-ray emission preparation command from the user via the partially pressed button. Furthermore, the X-ray apparatus 100 may receive the X-ray emission command from the user via the fully pressed button.

The X-ray apparatus 100 may control an operation of a protection circuit for protecting the lithium ion battery 334 during X-ray emission (S1103). In detail, during the X-ray emission, the lithium ion battery 334 may become transiently over-discharged, enter an overcurrent state, be overheated, or become unbalanced between cells due to momentary overcurrent, which may cause the BMS 332 to unnecessarily operate the protection circuit. Thus, to prevent unnecessary operations of the protection circuit, the BMS 332 may control an operation of the protection circuit exceptionally during the X-ray emission.

According to an embodiment, when X-rays are emitted, the BMS 332 may change an overcurrent reference value and/or an over-discharge reference value for the lithium ion battery 334, which are used for operating the protection circuit. In other words, when the X-rays are emitted, the BMS 332 may increase a current reference value for operating the protection circuit due to the occurrence of overcurrent, compared to an existing current reference value, and/or decrease a voltage reference value for operating the protection circuit due to the occurrence of over-discharge, compared to an existing voltage reference value.

Furthermore, the X-ray apparatus 100 may change an overcurrent reference value and/or an over-discharge reference value based on an X-ray emission preparation signal. For example, if the input device 151 is formed as a hand switch, the X-ray apparatus 100 may acquire the X-ray emission preparation signal via a partially pressed button on the input device 151. Subsequently, the X-ray apparatus 100 may respectively change, based on an X-ray emission completion signal, the changed overcurrent reference value and the changed over-discharge reference value back to the same overcurrent and over-discharge reference values as before. For example, the X-ray apparatus 100 may acquire the X-ray emission completion signal from the high voltage generator of the X-ray apparatus 100. Similarly, when the X-ray emission occurs, the X-ray apparatus 100 may change an overheating reference value and/or a cell unbalancing reference value for the lithium ion battery 334, which are used for operating the protection circuit.

According to another embodiment, when the X-rays are emitted, the BMS the X-ray apparatus 100 may prevent the protection circuit from operating protection against over-discharge and/or overcurrent. In detail, the X-ray apparatus 100 may prevent the protection circuit from operating protection against over-discharge and/or overcurrent based on the X-ray emission preparation signal. Subsequently, the X-ray apparatus 100 may allow the protection circuit to operate to protect against the over-discharge or overcurrent based on the X-ray emission completion signal. Similarly, when the X-ray emission occurs, the X-ray apparatus 100 may prevent the protection circuit from operating protection against overheating and/or unbalancing between cells.

During the X-ray emission, the X-ray apparatus 100 may control charging of the lithium ion battery 334. In detail, the X-ray apparatus 100 may stop the charging based on the X-ray emission preparation signal. Subsequently, the X-ray apparatus 100 may resume the charging based on the X-ray emission completion signal.

Figure 12:
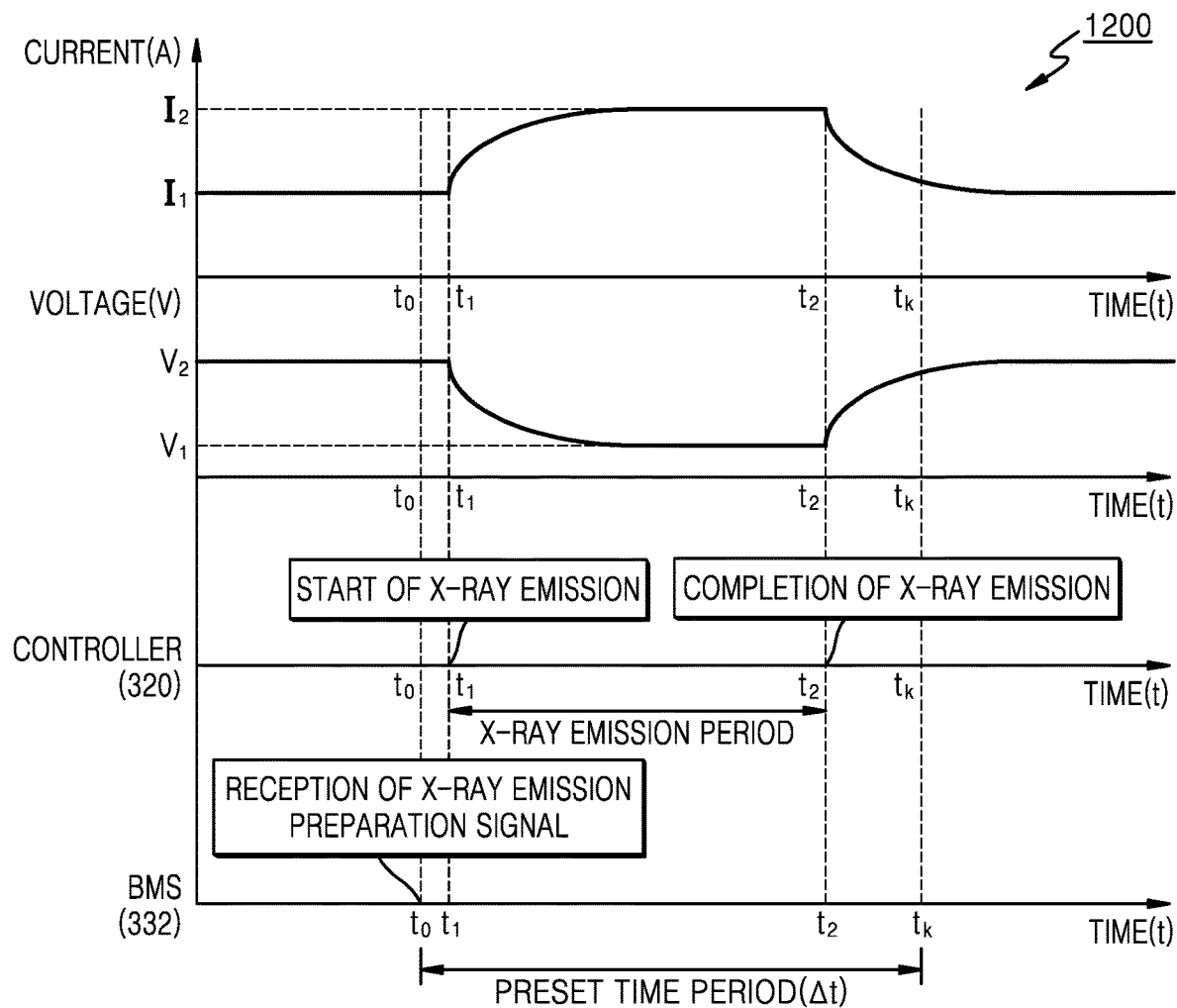
FIG. 12 illustrates variations in values of a current and a voltage of a lithium ion battery and operations of a controller and a BMS over various time periods, according to an embodiment.

FIG. 12 illustrates a timetable 1200 showing variations in values of a current and a voltage of the lithium ion battery 334 and operations of the controller 320 and the BMS 332 with respect to various time periods.

Referring to FIG. 12, the timetable 1200 includes variations in values of a current and a voltage of the lithium ion battery 334 and information about operations of the controller 320 and the BMS 332.

In the timetable 1200, the value of a current may vary according to an emission state of X-rays. In detail, the current may have a first current value $I_1$ at a zero-th time point $t_0$ when the BMS 332 receives an X-ray emission preparation signal from the controller 320. Subsequently, the value of current may start to increase rapidly towards a second current value $I_2$ at a first time point $t_1$ when the X-ray radiator (310 of FIG. 3) emits X-rays toward an object according to control by the controller 320. The current then reaches the second current value $I_2$ after the first time point $t_1$. The value of the current may then start to decrease back towards the first current value $I_1$ at a second time point $t_2$ when the X-ray radiator 310 completes X-ray emission according to an X-ray emission completion instruction from the controller 320. At the time $t_k$ it can be seen that current has decreased from the relatively high $I_2$ level. According to an embodiment, when the current of the lithium ion battery 334 increases to 40 A or more, the BMS 332 may recognize that the lithium ion battery 334 is in an overcurrent state. For example, the first current value $I_1$ may be 1 A, and the second current value $I_2$ may be 257 A.

The value of a voltage may also vary according to an emission state of X-rays. In detail, the voltage may have a second voltage value $V_2$ at the zero-th time point $t_0$. The BMS 332 receives an X-ray emission preparation signal from the controller 320 at a zero-th time point $t_0$. Subsequently, the value of voltage may start to decrease rapidly towards a first voltage value $V_1$ at the first time point $t_1$ when the X-ray radiator 310 starts to emit X-rays toward the object according to control by the controller 320. The value of the voltage then reaches the first voltage value $V_1$ after the first time point $t_1$. The value of a voltage may then increase back to the second voltage value $V_2$ after the second time point $t_2$ when the X-ray radiator 310 completes X-ray emission according to an X-ray emission completion instruction from the controller 320. At the time $t_k$ it can be seen that voltage has increased from the lower $V_1$ voltage level. According to an embodiment, when the voltage of the lithium ion battery 334 decreases to 275V or less, the BMS 332 may recognize that the lithium ion battery 334 is in an over-discharged state. For example, the first voltage value $V_1$ may be 204V, and the second voltage value $V_2$ may be 302V.

The BMS 332 may receive an X-ray emission preparation signal from the controller 320 at the zero-th time point $t_0$. The BMS 332 may control a protection circuit not to operate during a preset time period $\Delta t$ from the zero-th time point $t_0$ when the BMS 332 receives the X-ray emission preparation signal. The preset time period $\Delta t$ may be 10 seconds, but is not limited thereto. The BMS 332 may control the protection circuit to resume protection at a k-th time point $t_k$ when the preset time period $\Delta t$ elapsed from the zero-th time point $t_0$.

The controller 320 may control the X-ray radiator 310 to emit X-rays onto the object at the first time point $t_1$. In other words, X-rays may be emitted onto the object at the first time point $t_1$. The controller 320 may control the X-ray radiator 310 to complete X-ray emission at the second time point $t_2$ that is before the k-th time point $t_k$.

Referring to the timetable 1200 of FIG. 12, the lithium ion battery 334 may transiently fall into an over-discharged state and/or an overcurrent state due to an instantaneous overcurrent at the first time point $t_1$ when the X-ray radiator 310 emits X-rays onto the object. This may cause the BMS 332 to unnecessarily operate the protection circuit. In this case, by operating the protection circuit, X-ray emission may not occur.

However, the lithium ion battery 334 inevitably enters an over-discharged state and/or an overcurrent state during X-ray emission. When the protection circuit operates to prevent this, X-ray emission may not occur. Thus, according to an embodiment, to prevent unnecessary operations of the protection circuit, the X-ray apparatus 100 may operate such that the BMS 332 controls the protection circuit not to operate during the preset time period $\Delta t$ starting from the zero-th time point $t_0$ when the X-ray emission preparation signal is received. The preset time period $\Delta t$ may end at k-th time point $t_k$.

According to another embodiment, the BMS 332 may prevent the protection circuit from operating during the preset time period $\Delta t$ starting from the first time point $t_1$ that is a time point when the controller 320 controls the X-ray radiator 310 to start X-ray emission.

Figure 13:
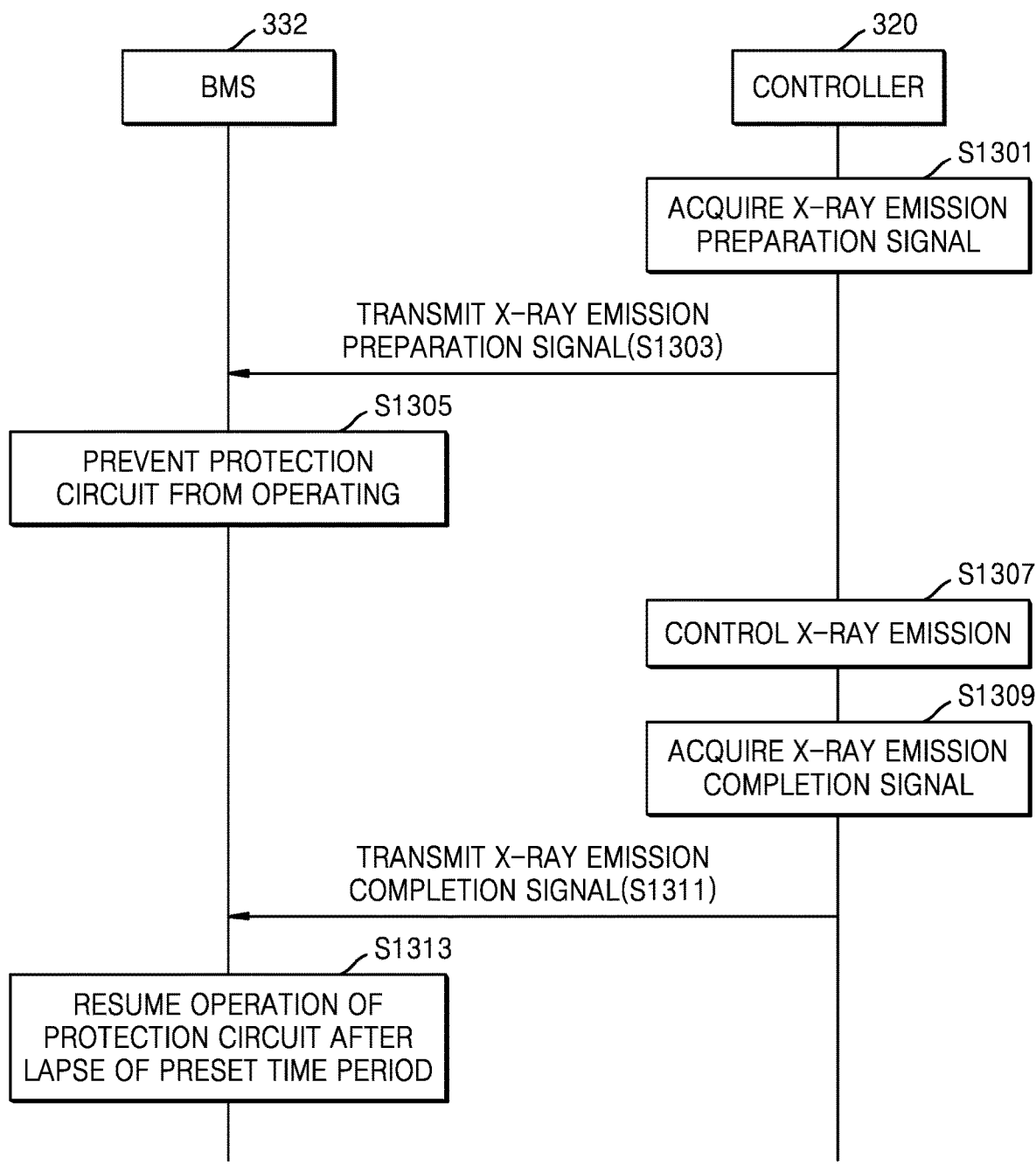
FIG. 13 is a flowchart of a method, performed by a BMS, of controlling an operation of a protection circuit during X-ray emission, according to an embodiment.

FIG. 13 is a flowchart of a method, performed by the BMS 332, of controlling an operation of a protection circuit during X-ray emission, according to an embodiment.

Referring to FIG. 13, the controller 320 acquires an X-ray emission preparation signal (S1301). According to an embodiment, the controller 320 may acquire the X-ray emission preparation signal via the input device (151 of FIG. 1). For example, when the input device 151 is formed as a two-step push hand switch, a user may press a button on the two-step push hand switch, which is the input device 151, to a first step indicating an X-ray emission command, and the controller 320 may receive the X-ray emission preparation signal through pressing of the button on the input device 151 to the first step.

The controller 320 transmits the acquired X-ray emission preparation signal to the BMS 332 (S1303). According to an embodiment, the controller 320 may transmit the X-ray emission preparation signal to the BMS 332 via a communication interface. The communication interface could be wired or wireless. In other words, the controller 320 may transmit a control signal to the BMS 332 as a signal indicating preparation of X-ray emission. According to another embodiment, the BMS 332 may directly receive an X-ray emission preparation signal generated in the input device 151 as the control signal. In this case, the X-ray emission preparation signal may be transmitted to the BMS 332 without being generated by the controller 320.

The BMS 332 pauses an operation of a protection circuit at a time point when the X-ray emission preparation signal is received (S1305). According to an embodiment, the BMS 332 may prevent the protection circuit from operating during a preset time period from the time point when the X-ray emission preparation signal is received. For example, the preset time period may be 10 seconds, but is not limited thereto.

The controller 320 controls the X-ray radiator 310 to emit X-rays (S1307). According to an embodiment, when the user fully presses (to a second step) the button on the input device 151, which is already pressed to the first step, the controller 320 may then receive an X-ray emission signal and control the X-ray radiator 310 to emit X-rays.

As the X-rays are emitted, overcurrent may occur in the lithium ion battery 334. However, since the BMS 332 stops the operation of the protection circuit in operation S1305, the protection circuit does not operate to protect the lithium ion battery 334 even when the lithium ion battery 334 is in an overcurrent state and/or an over-discharged state. In other words, even when X-rays are emitted by the X-ray radiator 310, the BMS 332 is not turned off during a preset time period. Thus, since the BMS 332 may prevent unnecessary operations of the protection circuit, current may flow from the lithium ion battery 334 to the X-ray radiator 310 through a high voltage generator, causing X-rays generated by the X-ray radiator 310 to be emitted towards an object.

The controller 320 may control the X-ray radiator 310 to complete X-ray emission before a time point when a preset time period elapsed from the time point at which the X-ray emission preparation signal is transmitted to the BMS 332.

The controller 320 may acquire an X-ray emission completion signal (S1309). According to an embodiment, the controller 320 may acquire the X-ray emission completion signal from the high voltage generator or an X-ray detector of the X-ray apparatus 100. Furthermore, according to another embodiment, when the user has not pressed a button on the input device 151 for a specific amount of time, or as soon as the user releases the button on the input device 151, the controller 320 may receive a signal indicating the completion of X-ray emission.

The controller 320 may transmit the acquired X-ray emission completion signal to the BMS 332 (S1311). According to an embodiment, the controller 320 may transmit a control signal generated based on the X-ray emission completion signal to the BMS 332 via the communication interface. The BMS 332 may receive the X-ray emission completion signal from the controller 320 before a preset time period elapses from the time point when the X-ray emission preparation signal is received.

The BMS 332 resumes an operation of the protection circuit at a time point that occurs a preset time period after the time point at which the operation of the protection circuit is paused in operation S1305 (S1313).

Figure 14:
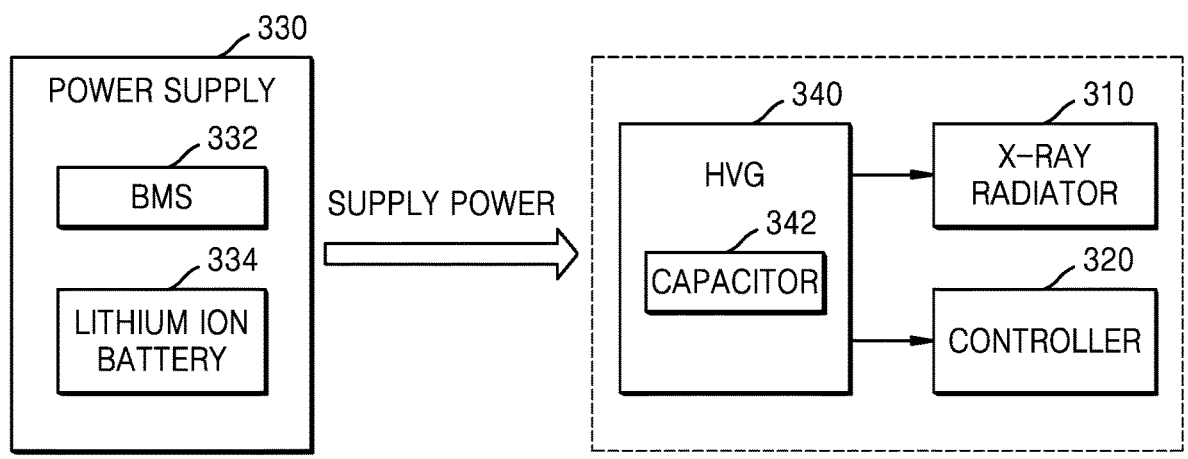
FIG. 14 is a block diagram of an X-ray apparatus according to an embodiment.

FIG. 14 is a block diagram of an X-ray apparatus 100 according to an embodiment.

Unlike the X-ray apparatus 100 described with reference to FIG. 3, the X-ray apparatus 100 of FIG. 14 further includes a high voltage generator 340. Since components of the X-ray apparatus 100 of FIG. 14, other than the high voltage generator 340, may respectively correspond to those of the X-ray apparatus 100 of FIG. 3, descriptions already provided above with respect to FIG. 3 will be omitted below. The same reference numerals denote the same elements.

Referring to FIG. 14, the high voltage generator 340 may receive power output from the lithium ion battery 334, amplify the received power, and supply the resulting power to the X-ray radiator 310 and the controller 320. The high voltage generator 340 may be electrically connected to the lithium ion battery 334. A larger amount of power than that consumed in an idle state is required to emit X-rays via the X-ray radiator 310. The high voltage generator 340 may amplify the power received from the lithium ion battery 334 to provide the resulting power to the X-ray radiator 310 during X-ray emission.

The high voltage generator 340 may include at least one capacitor 342. According to an embodiment, the at least one capacitor 342 may be electrically connected in parallel to the lithium ion battery 334.

The at least one capacitor 342 may charge an internal charge of the at least one capacitor 342 (i.e., be charged) by using a power received from the lithium ion battery 334, and supply the power to the X-ray radiator 310 by using a discharge voltage. The at least one capacitor 342 may supply power to the X-ray radiator 310 through the discharge voltage while the X-ray radiator 310 emits X-rays onto an object based on an X-ray emission preparation signal received from the controller 320. During X-ray emission by the X-ray radiator 310, the power may be supplied to the X-ray radiator 310 not directly from the lithium ion battery 334 but via a discharge voltage at the at least one capacitor 342, thereby preventing degradation due to voltage drops across the lithium ion battery 334.

According to an embodiment, the high voltage generator 340 may include two (2) capacitors 342, but the number of the at least one capacitor 342 is not limited thereto. The at least one capacitor may each have a capacitance less than or equal to 10,000 micro-farads (μF). According to an embodiment, the X-ray apparatus 100 may include the lithium ion battery having a smaller volume than a lead-acid battery, and the high voltage generator 340 may include two capacitors 342, each having a capacitance less than or equal to 10,000 μF, thereby allowing efficient spatial arrangements. Thus, the X-ray apparatus 100 may be implemented with a small size and a compact design.

Embodiments may be implemented through non-transitory computer-readable recording media having recorded thereon computer-executable instructions and data. The instructions may be stored in the form of program codes, and when executed by a processor, generate a predetermined program module to perform a specific operation. Furthermore, when being executed by the processor, the instructions may perform specific operations according to the embodiments.

Furthermore, embodiments may be implemented as a software program including instructions stored in computer-readable storage media. The computer-readable storage media may be provided in the form of non-transitory storage media. The term 'non-transitory' only means that the storage media do not include signals and are tangible media, and does not distinguish whether data is semi-permanently or temporarily stored on the storage media.

In addition, methods of operating an X-ray apparatus according to embodiments may be included in a computer program product when provided. The computer program product may be traded as a commodity between a seller and a buyer.

The computer program product may include a software program and a computer-readable storage medium having the software program stored thereon. For example, the computer program product may include goods (e.g., downloadable apps) in the form of a software program electronically distributed via a manufacturer of an X-ray apparatus or an electronic market (e.g., Google Play Store and App Store). For electronic distribution, at least some software programs may be stored in storage media or may be created temporarily. In this case, the storage media may be storage media contained in a relay server for temporarily storing a software program, a manufacturer's server, or a server of an electronic market.

The computer program product may include a storage medium of a server or a terminal in a system composed of the server and the terminal (e.g., the X-ray apparatus 100). Alternatively, when a third device (e.g., a smartphone) is connected to a server or terminal through a communication network, the computer program product may include a storage medium of the third device. Alternatively, the computer program product may include a software program that is transmitted from a server to a terminal or a third device or from the third device to the terminal.

In this case, one of the server, the terminal, and the third device may run the computer program product to perform methods according to embodiments. Alternatively, two or more of the server, the terminal, and the third device may run the computer program product to implement methods according to embodiments in a distributed manner.

For example, a server (e.g., a cloud server or an artificial intelligence (AI) server) may run a computer program product stored thereon to control a terminal connected to the server through a communication network to perform methods according to embodiments.

As another example, a third device may run a computer program product to control a terminal connected to the third device through a communication network to perform methods according to embodiments.

When a third device runs the computer program product, the third device may download the computer program product from a server and execute the downloaded computer program product. Alternatively, the third device may run a preloaded computer program product to perform methods according to embodiments.

While one or more embodiments have been described with reference to the figures, it will be understood by those of ordinary skill in the art that various changes in form and details may be made therein without departing from the spirit and scope of the present disclosure as defined by the following claims. Accordingly, the above embodiments and all aspects thereof are examples only and are not limiting.

What is claimed is:

1. A mobile X-ray apparatus comprising:
   an X-ray radiator;
   a controller configured to control the X-ray radiator;
   a lithium ion battery configured to supply an operating power to the X-ray radiator and the controller;
   a protection circuit configured to protect the lithium ion battery against overcurrent or over-discharge; and
   a battery management system (BMS) configured to control an operation of the protection circuit based on status information of the lithium ion battery,
   wherein the BMS is further configured to receive an X-ray emission preparation signal from the controller and prevent the protection circuit from operating during a preset time period starting from a time point at which the X-ray emission preparation signal is received by the BMS.

2. The mobile X-ray apparatus of claim 1, wherein the BMS is further configured to resume the operation of the protection circuit when the preset time period ends.

3. The mobile X-ray apparatus of claim 1, wherein the controller is further configured to control the X-ray radiator to complete X-ray emission before a second time point that occurs the preset time period after a first time point at which the X-ray emission preparation signal is transmitted to the BMS.

4. The mobile X-ray apparatus of claim 3, wherein the BMS is further configured to receive an X-ray emission completion signal from the controller before the second time point.

5. The mobile X-ray apparatus of claim 4, further comprising at least one capacitor configured to be charged by using a power from the lithium ion battery, and supply a power to the X-ray radiator by using a discharge voltage.

6. The mobile X-ray apparatus of claim 5, wherein the at least one capacitor is further configured to supply the power to the X-ray radiator by using the discharge voltage while the X-ray radiator emits X-rays toward an object based on the X-ray emission preparation signal received from the controller.

7. The mobile X-ray apparatus of claim 5, wherein each of the at least one capacitor has a capacitance less than or equal to 10,000 micro-farads ($\mu F$).

8. The mobile X-ray apparatus of claim 5, wherein the at least one capacitor comprises two capacitors.

9. The mobile X-ray apparatus of claim 1, wherein the BMS and the controller each include a communication interface, and the BMS and the controller communicate with each other via the communication interfaces.

10. A method of operating a mobile X-ray apparatus comprising a lithium ion battery, the method comprising:
    receiving an instruction for X-ray emission preparation from a user;
    preventing a protection circuit from operating for protection of the lithium ion battery during a preset time period starting from a time point at which the instruction is received; and
    emitting X-rays toward an object based on the received instruction.

11. The method of claim 10, further comprising resuming an operation of the protection circuit after a time point that occurs when the preset time period ends.

12. The method of claim 10, wherein the emitting of the X-rays toward the object comprises completing the X-ray emission before a time point that occurs the preset time period after the time point at which the instruction is received.

13. A computer program product comprising a non-transitory computer-readable storage medium having recorded thereon a method of operating a mobile X-ray apparatus including a lithium ion battery, wherein the non-transitory computer-readable storage medium comprises instructions which, when executed by the mobile X-ray apparatus, cause the mobile X-ray apparatus to perform the method comprising:
- receiving an instruction for X-ray emission preparation from a user;
- preventing a protection circuit from operating for protection of the lithium ion battery during a preset time period from a time point at which the instruction is received; and
- emitting X-rays toward an object based on the received instruction.

* * * * *